US011118211B2

(12) United States Patent
Chakrabarti et al.

(10) Patent No.: US 11,118,211 B2
(45) Date of Patent: Sep. 14, 2021

(54) METHODS FOR THE DESIGN OF MECHANISM-BASED SIRTUIN ACTIVATING COMPOUNDS

(71) Applicant: CHAKRABARTI ADVANCED TECHNOLOGY LLC, Mt. Laurel, NJ (US)

(72) Inventors: Raj Chakrabarti, Moorestown, NJ (US); Alok Upadhyay, Mount Laurel, NJ (US); Sudipto Munshi, Philadelphia, PA (US); Suyambu Kesava Vijayan Ramaswamy, Marlton, NJ (US); Xiangying Guan, Cherry Hill, NJ (US)

(73) Assignee: CHAKRABARTI ADVANCED TECHNOLOGY LLC, Mt. Laurel, NJ (US)

( * ) Notice: Subject to any disclaimer, the term of this patent is extended or adjusted under 35 U.S.C. 154(b) by 0 days.

(21) Appl. No.: 16/986,858

(22) Filed: Aug. 6, 2020

(65) Prior Publication Data
US 2020/0370089 A1 Nov. 26, 2020

Related U.S. Application Data

(63) Continuation of application No. 15/759,646, filed as application No. PCT/US2016/051726 on Sep. 14, 2016.

(60) Provisional application No. 62/218,460, filed on Sep. 14, 2015.

(51) Int. Cl.
*C12Q 1/34* (2006.01)
*C12Q 1/48* (2006.01)
*C12N 9/10* (2006.01)
*G01N 33/50* (2006.01)
*G01N 33/573* (2006.01)

(52) U.S. Cl.
CPC .............. *C12Q 1/34* (2013.01); *C12N 9/10* (2013.01); *C12Q 1/48* (2013.01); *C12Y 305/01098* (2013.01); *G01N 33/502* (2013.01); *G01N 33/5014* (2013.01); *G01N 33/5735* (2013.01); *G01N 2333/91* (2013.01); *G01N 2333/98* (2013.01); *G01N 2500/04* (2013.01)

(58) Field of Classification Search
CPC ... C12Q 1/34; C12Q 1/48; C12N 9/10; C12Y 305/01098; G01N 33/5014; G01N 33/502; G01N 33/5735; G01N 2333/91; G01N 2333/98; G01N 2500/04
USPC ........................................................ 702/19
See application file for complete search history.

(56) References Cited

U.S. PATENT DOCUMENTS

2009/0137681 A1* 5/2009 Sinclair ................ C07C 255/61
514/603

* cited by examiner

*Primary Examiner* — Jerry Lin
(74) *Attorney, Agent, or Firm* — J. Clinton Wimbish; Nexsen Pruet, PLLC

(57) ABSTRACT

The instant invention provides workflows for the design and characterization of mechanism-based sirtuin modulating compounds, including new or improved sirtuin activating compounds. Workflows for the design of mechanism-based sirtuin activating compounds are provided, based on conditions that must be satisfied by activators if they are to exploit the common catalytic mechanism of all sirtuin enzymes and hence increase catalytic efficiency for any sirtuin and any substrate.

20 Claims, 14 Drawing Sheets

ADPR-Pr-Im: ADPR peptidyl-Imidate

METHODS FOR THE DESIGN OF MECHANISM-BASED SIRTUIN ACTIVATING COMPOUNDS

RELATED APPLICATION DATA

The present application is a continuation application of U.S. patent application Ser. No. 15/759,646 filed Mar. 13, 2018 which is a U.S. National Phase of PCT/US2016/051726, filed Sep. 14, 2016, which claims priority pursuant to 35 U.S.C. § 119(e)(1) to U.S. Provisional Application Ser. No. 62/218,460 filed Sep. 14, 2015 which is incorporated herein by reference in its entirety.

BACKGROUND

Sirtuin (silent information regulator) enzymes, which catalyze NAD+-dependent protein post-translational modifications, have emerged as critical regulators of many cellular pathways. In particular, these enzymes protect against age-related diseases and serve as key mediators of longevity in evolutionarily distant organismic models. Sirtuins are $NAD^+$-dependent lysine deacylases, requiring the cofactor $NAD^+$ to cleave acyl groups from lysine side chains of their substrate proteins.

A thorough understanding of sirtuin chemistry is not only of fundamental importance, but also of considerable medicinal importance, since there is enormous current interest to develop new mechanism-based sirtuin modulators. The mechanism of sirtuin-catalyzed, $NAD^+$-dependent protein deacylation is depicted in FIG. 1. Its overall catalytic process has been suggested to proceed in two consecutive stages. The initial stage involves the cleavage of the nicotinamide moiety of NAD+ and the nucleophilic attack of the acetyl-Lys side chain of the protein substrate to form a positively charged O-alkylimidate intermediate. Nicotinamide-induced reversal of the intermediate (the so-called base exchange reaction) causes reformation of $NAD^+$ and acetyl-Lys protein. The energetics of this reversible reaction affects both the potency of nicotinamide (NAM) inhibition of sirtuins and the Michaelis constant for NAD+ ($K_{m,NAD+}$). The second stage of sirtuin catalysis, which includes the rate determining step, involves four successive steps that culminate in deacetylation of the Lys side chain of the protein substrate and the formation of O-acetyl ADP ribose coproduct.

Recently, in order to combat old age, intense interest has developed in the activation of the seven mammalian sirtuin enzymes (SIRT1-7). Compared to enzyme inhibitors, which constitute the vast majority of today's drugs, enzyme activators have considerable advantages. However, they are much more difficult to design, because enzymatic catalysis has been optimized over billions of years of evolution. Prior work on sirtuin activation has focused exclusively on experimental screening, with an emphasis on allosteric activation of the SIRT1 enzyme. Indeed, small molecule allosteric activators of SIRT1 have been demonstrated to induce lifespan extension in model organisms such as mice. Allosteric activation is one of four known modes by which small molecules can activate enzymes. They function by decreasing the dissociation constant for the substrate (the acetylated protein dissociation constant $K_{d,Ac-Pr}$ for sirtuins).

Almost all known sirtuin activators allosterically target SIRT1 and do not bind in the active site. However, allosteric activators only work with certain substrates of SIRT1. It is now known that other sirtuins, including SIRT2, SIRT3 and SIRT6, play significant roles in regulating mammalian longevity. General strategies for the activation of any mammalian sirtuin (including activation of SIRT1 for other substrates) are hence of central importance, but not understood. In general, allosteric activation to decrease substrate $K_d$ will not be an option for enzyme activation, rending mechanism-based activation important.

Foundations for the rational design of mechanism-based activators have been lacking. Several types of mechanism-based sirtuin inhibitors have been reported recently in the literature, including Ex-527. However, mechanism-based activation has proven far more elusive, due to the difficulty in screening for the balance of properties needed for a modulator to bind the active site and accelerate catalysis. While there are many ways to inhibit an enzyme's mechanism, there are far fewer ways to activate it. Only a dozen or so distinct classes of small molecule enzyme activators are currently known, with only four known modes of activation across all families of enzymes. None of those modes of activation exploit the unique catalytic reaction mechanisms of the target enzymes.

Clearly, there is a need for a mechanism-based method to design sirtuin activating compounds.

SUMMARY

The instant invention provides kinetic models for activity modulation of sirtuin enzymes that are distinct from known modes of enzyme modulation. These models establish conditions that must be satisfied by activators if they are to exploit the common catalytic mechanism of all sirtuin enzymes and hence increase catalytic efficiency for any sirtuin and any substrate. Based on these models, the methods described herein can establish mechanism-based workflows for the design and characterization of mechanism-based sirtuin modulating compounds, including new or improved sirtuin activating compounds. These workflows are distinct from any previously reported enzyme activator or inhibitor drug discovery strategies.

BRIEF DESCRIPTION OF THE DRAWINGS

FIG. 3A illustrates mechanistic interpretation of double reciprocal plots for initial deacylation rates with NAM as a base exchange inhibitor. The substrate is NAD$^+$, and peptide is present in constant saturating concentrations. FIG. 3B provides double reciprocal plots for initial rates of SIRT3 deacylation rates with different concentrations of NAM depicting the corresponding parameters for this enzyme.

FIG. 5A illustrates double reciprocal plots for deacylation initial rate measurements in the presence of activator. The shaded box on the y-axis highlights the data that is used to construct the Dixon plot at saturating [NAD$^+$] depicted in FIG. 5B. FIG. 5B illustrated Dixon plots for deacylation initial rate measurements in the presence of activator. FIG. 5C provides a comparison of double reciprocal plots at [NAM]=0 uM in the presence and absence of activator. FIG. 5D provides a comparison of Dixon plots at 1/[NAD$^+$]=0 in the presence and absence of activator. "A" denotes a mechanism-based sirtuin activating compound.

FIG. 6A is N-Benzyl-3,5-dicarbethoxy-4-phenyl-1,4-dihydropyridine (DHP-1). FIG. 6B is N-Benzyl-3,5-dicarboxy-4-phenyl-1,4-dihydropyridine (DHP-2). FIG. 6C 5,3'-Diallyl-2,4'-dihydroxybiphenyl (Honokiol).

FIG. 7A illustrates $K_d$ for NAD$^+$ binding to SIRT3 enzyme in presence of 5% DMSO; FIG. 7B illustrates $K_d$ for Honokiol binding to SIRT3 enzyme in presence of 5% DMSO; FIG. 7C illustrates $K_d$ for Honokiol binding to SIRT3 enzyme: NAD+ complex in presence of 5% DMSO.

FIG. 8A details 10uM NAD$^+$ and 250 uM FdL2 peptide substrate (N=3). FIG. 8B details 3 mM NAD$^+$ and 3 uM FdL2 peptide substrate (N=4). FIG. 8C illustrates 500 uM NAD+ and 250 uM FdL2 peptide substrate (N=3).

FIG. 9A details 50 uM NAD$^+$ and 600 uM MnSOD K122 peptide substrate (N=3). FIG. 9B details 2.5 mM NAD$^+$ and 6.25 uM MnSOD K122 peptide substrate (N=5).

In FIG. 10A, x denotes $K_{m,NAD+,app}/K_{m,NAD+}$ whereas y denotes [NAD+]/$K_{m,NAD}$; In FIG. 10B, x denotes $K_{m,peptide,app}/K_{m,peptide}$ whereas y denotes [peptide]/$K_{m,peptide}$;

DETAILED DESCRIPTION

Embodiments described herein can be understood more readily by reference to the following detailed description, examples and drawings. Elements, apparatus, and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

In one aspect, the instant invention relates to models for activity modulation of sirtuin enzymes suitable for the design and characterization of mechanism-based sirtuin activating compounds (MB-STACs) that can activate any of the mammalian sirtuins SIRT1-7. To a greater extent than inhibitor design, rational activator design requires the use of a mechanistic model in the workflow. Efforts to design mechanism-based sirtuin activating compounds have been hindered by the lack of a complete steady state kinetic model of sirtuin catalysis that accounts for the effects of both NAD+ and NAM on enzyme activity. The instant invention provides a steady state model for sirtuin catalyzed deacylation that is suitable for a) investigation of the mode of action of mechanism-based sirtuin modulators, including activators; b) design of mechanism-based sirtuin activating compounds.

A tractable steady state model suitable for the purpose of mechanism-based sirtuin activator design must account for features of sirtuin catalysis such as the following:

The calculated free energy of activation for nicotinamide cleavage (ADP-ribosylation of the acyl-Lys substrate) in the bacterial sirtuin enzyme Sir2Tm as computed through mixed quantum/molecular mechanics (QM/MM) methods is 15.7 kcal mol$^{-1}$. An experimental value of 16.4 kcal mol$^{-1}$ for the activation barrier in the yeast sirtuin homolog Hst2 was estimated from the reaction rate 6.7 s$^{-1}$ of nicotinamide formation. The nicotinamide cleavage reaction is endothermic, with a computed ΔG of 4.98 kcal mol$^{-1}$ in Sir2Tm.

The calculated free energy of activation for the rate limiting chemistry step (collapse of the bicyclic intermediate) from QM/MM simulations is 19.2 kcal mol$^{-1}$ for Sir2Tm, in good agreement with the experimental value of 18.6 kcal/mol$^{-1}$ estimated from the $k_{cat}$ value of 0.170±0.006 s$^{-1}$ (0.2+/−0.03 s$^{-1}$ for Hst2).

The remaining steps in the catalytic cycle are significantly faster than the above steps. The other chemistry steps in stage 2 of the reaction are effectively irreversible, as is product release in the presence of saturating peptide concentrations.

Figure 2:
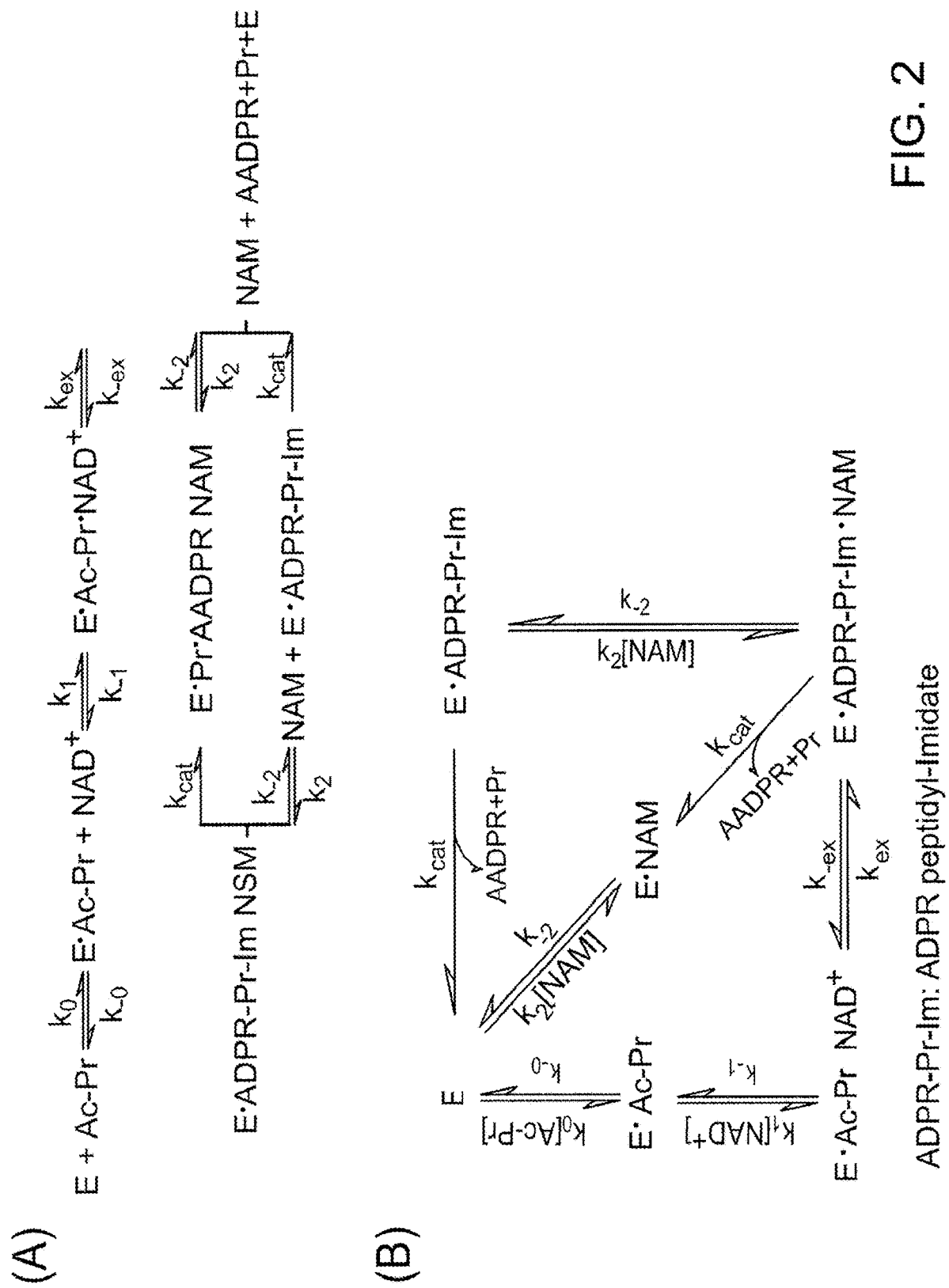
FIG. 2. General model for sirtuin-catalyzed deacylation in the presence of NAD+ and NAM. In the presence of saturating Ac-Pr, E is rapidly converted into E.Ac-Pr and NAM binding to E can be neglected, resulting in a simplified reaction network with 5 species. Ac-Pr, acetylated peptide; ADPR, adenosine diphosphate ribose; AADPR, O-acetyl-adenosine-diphosphate-ribose. For simplicity, deacylation and AADPR+Pr dissociation are depicted to occur together ($k_{cat}$ denotes the rate constant for the rate-limiting step of deacylation and dissociation of AADPR+Pr from E). This provides a minimal kinetic model that captures the essential features of sirtuin deacylation kinetics, suitable for a variety of applications including augmentation of the model to include the effects of mechanism-based modulators on sirtuin activity.

The kinetic models of the instant invention include representations of all steps in stage 1 of the reaction, including the nicotinamide cleavage/base exchange and nicotinamide binding steps. (Since all the steps in stage 2 are effectively irreversible, the full model including these steps can be immediately derived from the basic model through simple modifications.) Such a kinetic model is represented in FIG. 2. This Figure shows a general reaction scheme for sirtuin deacylation including base exchange inhibition. The reaction mechanism of sirtuins precludes the use of rapid equilibrium methods for the derivation of even an approximate initial rate model. Steady-state modeling is essential. In general, rapid equilibrium modeling requires that no step that is modeled, other than that being measured, is irreversible. In the instant case, the issue originates in the fact that the reverse (base exchange) reaction for the NAM cleavage step is not possible upon NAM dissociation; a lack of (or negligible) base exchange reaction rate prior to the rate limiting catalytic step (which always occurs at [NAM]=0) necessitates a steady state model. Such base exchange inhibition of sirtuins can be classified as hyperbolic mixed noncompetitive inhibition of deacylation.

A prerequisite for enzyme activation is that the modulator must co-bind with substrates—NAD+ and acylated peptide in the case of sirtuins. Within the context of enzyme inhibition, two modes of action display this property: noncompetitive and uncompetitive inhibition. Noncompetitive inhibitors bind with similar affinities to the apoenzyme and enzyme-substrate, enzyme-intermediate or enzyme-product complexes whereas uncompetitive inhibitors bind with significantly lower affinity to the apoenzyme. Both are specific examples of the more general notion of a mixed noncompetitive modulator that co-binds with substrates. Though some known sirtuin inhibitors may satisfy the requirement of cobinding with substrates, they do not possess other critical attributes necessary for mechanism-based enzyme activation. While such compounds may have promising properties as potential hits for the development of mechanism-based activators, prior studies have only characterized their kinetic effects in terms of traditional rapid equilibrium formulations of enzyme inhibition, rather than a steady-state formulation for mechanism-based enzyme modulation.

By identifying the biophysical properties that small molecules must have to function as mechanism-based activators, the models of the instant invention enable drug discovery of MB-STACs. More generally, they enable drug discovery of novel mechanism-based sirtuin modulating compounds with prescribed effects on the catalytic mechanism of the enzymes that lead to either activation or inhibition. In one embodiment, drug discovery is effected by i) screening a series of "test compounds" to identify a "hit compound," ii) validating a hit compound, iii) evolving the hit compound into a "lead compound," and iv) optimizing the lead compound.

Identification of a Hit Compound

In one aspect of the instant invention, a method for identifying a "hit compound" for a MB-STAC is provided. The method comprises decomposing the observed kinetic effects of a test compound into components and identifying those compounds that display favorable values as hit compounds.

Test compounds can be obtained by any manner known in the art. For example, compounds from a database of diverse drug-like chemical compounds can be synthesized or acquired. Test compounds can also be generated via virtual screening through molecular docking of a virtual library of compounds to a computer model of the sirtuin enzyme active site. For example, test compounds can be generated which show binding outside of the NAD+ binding site (the so-called A and C pockets).

In the identification method, the effects of nonsaturating or saturating concentrations of a test compound on steady-state and equilibrium parameters of a sirtuin enzyme are assayed, e.g., deacylation activity of a sirtuin enzyme and binding affinity of substrates/intermediates. Any sirtuin enzyme can be used, including sirtuin 1-7. Typically the enzyme is purified.

The method comprises incubating the test compound with a sirtuin enzyme, NAD+, NAM, and a saturating concentration of an acylated substrate peptide in an assay for deacylation activity. An example of substrate peptide is acetyl-coenzyme A synthetase 2. The initial rate and/or average rate of the sirtuin enzyme-catalyzed deacylation at several NAD+ concentrations for each of several NAM concentrations is measured.

The rate data is then fitted into the following nonlinear model:

$$\frac{v}{v_{max}} = \frac{[NAD^+]\left(1+\frac{[NAM]}{K_1}\right)}{K_{m,NAD^+}\left(1+\frac{[NAM]}{K_2}\right)+[NAD^+]\left(1+\frac{[NAM]}{K_3}\right)}$$

wherein v denotes initial deacylation rate, for both in the presence and in the absence of the test compound. From this non-linear model, estimates are obtained of the steady state parameters $v_{max}$, $K_{m,NAD+}$, $K_1$, $K_2$, $K_3$ in the absence of a test compound and $v_{max,app}$, $K_{m,NAD+,app}$, $K_{1,app}$, $K_{2,app}$, $K_{3,app}$ in the presence of a test compound at a nonzero concentrations.

Next a relationship is applied between the estimated steady state parameters and at least one of the following properties of the sirtuin enzyme:

$K_{d,NAD+}$, $K_{d,NAM}$, $K_{ex}$, $k_1$, $k_{-1}$, $k_2$, $k_{-2}$, $k_{ex}$, $k_{-ex}$, $k_{cat}$ wherein $K_{d,NAD+}$ is the dissociation constant for NAD+, $K_{d,NAM}$ is the dissociation constant for NAM, $K_{ex}$ is the exchange equilibrium constant, $k_1$,$k_{-1}$ are the on/off rate constants of NAD+ binding to enzyme-peptide substrate complex, $k_2$,$k_{-2}$ are the on/off rate constants of NAM binding, $k_{ex}$,$k_{-ex}$ are the nicotinamide cleavage and base exchange rate constants, and $k_{cat}$ is the rate constant of the rate limiting step of subsequent steps of deacylation and product/coproduct release.

These relationships can be obtained as follows. First, the rate equations for the reaction network in FIG. 2 enable the derivation of steady-state conditions for the reaction. Solving the linear system of algebraic equations for the steady-state concentrations

[E.Ac-Pr],[E.Ac-Pr.NAD$^+$],[E.ADPR-Ac-Im.NAM], [E.ADPR-Ac-Im],[E.NAM]

in terms of the rate constants and [NAD+],[NAM], which are assumed to be in significant excess and hence approximately equal to their initial concentrations $[NAD^+]_0$, $[NAM]_0$ respectively, expressions of the form are obtained:

$$[E.Ac\text{-}Pr]/[E]_0 = c_{11} + c_{12}[NAM]$$

$$[E.Ac\text{-}Pr.NAD^+]/[E]_0 = c_{21}[NAD^+] + c_{22}[NAD^+][NAM]$$

$$[E.ADPR\text{-}Ac\text{-}Im.NAM]/[E]_0 = c_{31}[NAD^+] + c_{32}[NAD^+][NAM] \quad (2)$$

$$[E.ADPR\text{-}Ac\text{-}Im]/[E]_0 = c_{41}[NAD^+]$$

$$[E.Ac\text{-}Pr.NAM]/[E]_0 = c_{51}[NAD^+] + c_{52}[NAM] + c_{53}[NAD^+][NAM] + c_{54}[NAM]^2$$

where the term $c_{54}$ that is second order in [NAM] is omitted from the analysis below and $$c_{11} = k_{cat}k_{-2}[k_{cat}k_{ex} + k_{cat}k_{-1} + k_{ex}k_{-2} + k_{-1}k_{-2} + k_{-ex}k_{-1}]$$

$$c_{12} = k_2 k_{-ex} k_{-1} k_{-2} + k_{cat}(k_{ex}k_{-2}k_2 + k_{-1}k_{-2}k_2)$$

$$c_{21} = k_{cat}(k_{-2}k_1 k_{cat} + k_{-2}k_1 k_{-2} + k_{-2}k_1 k_{-ex})$$

$$c_{22} = k_1 k_2 k_{-ex} k_{-2} + k_{cat} k_1 k_2 k_{-2}$$

$$c_{31} = k_{cat} k_1 k_{ex} k_{-2}$$

$$c_{32} = k_1 k_{ex} k_2 k_{-2}$$

$$c_{41} = k_1 k_{ex} k_{-2} k_{-2}$$

$$c_{51} = k_{cat} k_1 k_{ex} k_{cat} \quad (3)$$

$$c_{52} = k_{cat}(k_{cat}k_2 k_{ex} + k_{cat}k_{-1}k_2 + k_{-2}k_2 k_{ex} + k_{-2}k_{-1}k_2 + k_{-ex}k_{-1}k_2)$$

$$c_{53} = k_{cat} k_1 k_{ex} k_2$$

$$c_{54} = k_{-ex} k_{-1} k_2 k_2 + k_{cat}(k_{ex}k_2 k_2 + k_{-1}k_2 k_2)$$

Using the expressions for the steady state species concentrations in the equation $$v = k_{cat}([E.ADPR-Pr-Im.NAM] + [E.ADPR-Pr-Im]) \quad (4)$$

$$= \frac{k_{cat}\left(\frac{[E.ADPR-Pr-Im.NAM]}{[E]_0} + \frac{[E.ADPR-Pr-Im]}{[E]_0}\right)[E]_0}{([E.Ac-Pr] + [E.Ac-Pr.NAD^+] + [E.ADPR-Ac-Im.NAM] + [E.ADPR-Ac-Im] + [E.NAM])\frac{1}{[E]_0}}$$

the rate law (1) is obtained with $$v_{max} = \frac{k_{cat}(c_{31} + c_{41})}{c_{21} + c_{31} + c_{41} + c_{51}}[E]_0 \quad (5)$$

$$K_{m,NAD^+} = \frac{c_{11}}{c_{21} + c_{31} + c_{41} + c_{51}}$$

$$\frac{1}{K_1} = \frac{c_{32}}{c_{31} + c_{41}}$$

$$\frac{1}{K_2} = \frac{1}{K_{m,NAD^+}} \frac{c_{12} + c_{52}}{c_{21} + c_{31} + c_{41} + c_{51}}$$

$$\frac{1}{K_{2'}} = \frac{1}{K_{m,NAD^+}} \frac{c_{54}}{c_{21} + c_{31} + c_{41} + c_{51}}$$

$$\frac{1}{K_3} = \frac{c_{22} + c_{32} + c_{53}}{c_{21} + c_{31} + c_{41} + c_{51}}$$

Relationships between the estimated steady-state parameters and kinetic or thermodynamic properties of the sirtuin enzyme then follow from (5).

In one embodiment, the relationship is selected from the following:

$$v_{max} \approx k_{cat}[E]_0$$

$$K_{m,NAD^+} \approx k_{cat}\left(\frac{1}{k_1} + K_{d,NAD+}\frac{k_{-2} + k_{-ex}}{k_{-2}k_{ex}}\right)$$

$$\frac{1}{K_1} \approx \frac{1}{K_{d,NAM}}$$

$$\frac{1}{K_2} \approx \frac{K_{d,NAD^+} K_{ex}}{K_{m,NAD^+} K_{d,NAM}}$$

$$\frac{1}{K_3} = \frac{1}{\alpha K_2} \approx \frac{1 + K_{ex}}{K_{d,NAM}}$$

wherein $[E]_0$ denotes the total sirtuin enzyme concentration, wherein the relationship relates the steady state parameters of the sirtuin enzyme to the dissociation, equilibrium and rate constants of the deacylation.

In another embodiment, the relationship $$v_{max} = \frac{k_{cat} * k_1 k_{ex} k_{-2}(k_{-2} + k_{cat})}{k_{-2}k_1 k_{ex}k_{-2} + k_{cat}(k_{-2}k_{cat}k_1 + k_{-2}k_{-2}k_1 + k_{-2}k_1 k_{-ex} + k_{-2}k_1 k_{ex} + k_1 k_{ex} k_{cat})}[E]_0$$

relates $v_{max}$ to rate constants of the sirtuin deacylation.

In another embodiment, the relationship $$K_{m,NAD^+} = \frac{k_{cat}k_{-2}[k_{ex}k_{cat} + k_{-1}k_{cat} + k_{ex}k_{-2} + k_{-1}k_{-2} + k_{-ex}k_{-1}]}{k_{-2}k_1 k_{ex}k_{-2} + k_{cat}(k_{-2}k_{cat}k_1 + k_{-2}k_{-2}k_1 + k_{-2}k_1 k_{-ex} + k_{-2}k_1 k_{ex} + k_1 k_{ex} k_{cat})}$$

relates $K_{m,NAD+}$ to rate constants of the sirtuin deacylation

In another embodiment, the relationship $$\frac{1}{K_1} = \frac{k_2}{k_{-2} + k_{cat}}$$

relates $1/K_1$ to rate constants of the sirtuin deacylation.

In another embodiment, the relationship $$\frac{1}{K_2} = \frac{1}{K_{m,NAD^+}} \frac{k_2 k_{-ex}k_{-1}k_{-2} + k_{cat}(k_2 k_{ex}k_{cat} + k_{-1}k_2 k_{cat} + k_{-ex}k_{-1}k_2 + 2k_{-2}k_2 k_{ex} + 2k_{-2}k_2 k_{-1})}{k_{-2}k_1 k_{ex}k_{-2} + k_{cat}(k_{-2}k_{cat}k_1 + k_{-2}k_{-2}k_1 + k_{-2}k_1 k_{-ex} + k_{-2}k_1 k_{ex} + k_1 k_{ex} k_{cat})}$$

relates $1/K_2$ to rate constants of the sirtuin deacylation.

In another embodiment, the relationship $$\frac{1}{K_3} = \frac{k_1 k_2 k_{-2}(k_{-ex} + k_{ex}) + k_{cat} k_1 k_2 (k_{-2} + k_{ex})}{k_1 k_{-2} k_{-2} k_{ex} + k_{cat}(k_{-2} k_{cat} k_1 + k_{-2} k_{-2} k_1 + k_{-2} k_1 k_{-ex} + k_{-2} k_1 k_{ex} + k_1 k_{ex} k_{cat})}$$

relates $1/K_3$ to rate constants of the sirtuin deacylation.

In another embodiment, the relationship $$\alpha K_{m,NAD+} = \frac{k_2 k_{-ex} k_{-1} k_{-2} + k_{cat}(k_2 k_{ex} k_{cat} + k_{-1} k_2 k_{cat} + k_{-ex} k_{-1} k_2 + 2 k_{-2} k_2 k_{ex} + 2 k_{-2} k_2 k_{-1})}{k_1 k_2 k_{-2}(k_{-ex} + k_{ex}) + k_{cat} k_1 k_2 (k_{-2} + k_{ex})}$$

relates $\alpha K_{m,NAD+}$ to the rate constants of the sirtuin deacylation.

Graphical representation of equation (1) is typically done in terms of either double reciprocal plots at constant [NAM] or Dixon plots at constant [NAD+]. In the former case, the slope of the plot (1/v vs 1/[NAD+]) at $$[NAM] = 0 \text{ is } \frac{K_{m,NAD^+}}{v_{max}},$$

for which the expression is:

$$\frac{K_{m,NAD^+}}{v_{max}} \approx \frac{1}{[E]_0}\left(\frac{1}{k_1} + k_{d,NAD+}\frac{k_{-2} + k_{-ex}}{k_{-2} k_{ex}}\right) \approx \frac{K_{m,NAD^+}}{k_{cat}[E]_0} \quad (6)$$

whereas for Dixon plot, the expression for the slope at 1/[NAD+]=0 is:

$$\frac{1}{K_3}\frac{1}{v_{max}} \approx \frac{1 + K_{ex}}{K_{d,NAM}}\frac{1}{k_{cat}[E]_0} \quad (7)$$

From equation (6), we see that catalytic efficiency of sirtuins cannot be improved by increasing $k_{cat}$. $k_{cat}/K_m$ does not change due to $k_{cat}$ modulation. Hence acceleration of product release does not constitute a general strategy for increasing $k_{cat}$ of sirtuins. However, other types of mechanism-based modulators can easily be accommodated within an extended framework that includes stage 2 of the reaction.

The kinetics of the nicotinamide cleavage reaction and the rate limiting step of deacylation both play essential roles in determining the value of $K_{m,NAD+}$. Note that in rapid equilibrium models of enzyme kinetics, which are not applicable to sirtuins, $K_m \approx K_d$. The difference between $K_{d,NAD+}$ and $K_{m,NAD+}$ has important implications for mechanism-based activation of sirtuins by small molecules. In particular, decrease of $K_{m,NAD+}$ independently of $K_{d,NAD+}$ can increase the activity of sirtuins at [NAM]=0. The kinetic model above establishes foundations for how this can be done.

The steady state parameter $\alpha$, which is a measure of the extent of competitive inhibition by the endogenous inhibitor NAM against the cofactor NAD+, can be expressed in terms of the ratio of $K_{d,NAD+}$ and $K_{m,NAD+}$:

$$\alpha = \frac{K_3}{K_2} \approx \frac{K_{d,NAD+}}{K_{m,NAD+}}\frac{K_{ex}}{1 + K_{ex}} \quad (8)$$

thus demonstrating how the kinetics of inhibition of deacylation by NAM can reveal differences in NAD+ binding affinity and nicotinamide cleavage rates among sirtuins. Given that $K_{ex}$ is generally >>1 for sirtuins, it is apparent from eqn (8) that the difference in magnitudes of $K_{d,NAD+}$ and $K_{m,NAD+}$ for sirtuins is captured by $\alpha$. $K_{m,NAD+}$, not $K_{d,NAD+}$ alone, determines the sensitivity of sirtuin activity to NAD+, and can vary substantially across this family of enzymes. The initial rate model and the definition of $\alpha$ allow $K_{d,NAD+}$ to be estimated (under suitable approximations) by steady state deacylation experiments that vary [NAM] as well as [NAD+].

In addition to the kinetic assays, optionally, the binding affinity of NAD+ to the complex of enzyme and the test compound and the binding affinity of NAD+ to the complex of enzyme, deacylated peptide and the test compound may be measured. In one embodiment, the binding affinity is determined by isothermal calorimetry or microscale thermophoresis.

The test compound is identified as a hit compound if the ratio of the value of the parameters obtained from the assay in the presence of the test compound to the value in the absence of the test compound satisfies specific constraints. These constraints are obtained through the following analysis.

In the so-called "NAD+" world" picture of global metabolic regulation, the intracellular concentrations of the sirtuin cofactor NAD+—which can vary with age—play a central role in regulating mammalian metabolism through sirtuin-dependent pathways. Due to the comparatively high Michaelis constants for NAD+ ($K_{m,NAD+}$'s) of mammalian sirtuins, their activities are sensitive to intracellular NAD+ levels.

The systemic decrease in NAD+ levels that accompanies organismic aging downregulates sirtuin activity and has been identified as central factor leading to various types of age-related health decline, whereas increases in NAD+ levels can upregulate sirtuin activity and as a result mitigate or even reverse several aspects of this decline. As such, NAD+ supplementation has emerged as a promising alternative to allosteric activation of sirtuins. Unlike allosteric activators like resveratrol, which are SIRT1-specific and have not been successfully applied to other sirtuins, NAD+ supplementation can activate most mammalian sirtuins in a substrate-independent fashion. Moreover, allosteric activators cannot fully compensate for reduction in sirtuin activity that occurs through NAD+ decline during aging. On the other hand, the effects of NAD+ supplementation are not specific to sirtuins and prohibitively high concentrations of NAD+, along with associated undesirable side effects, may be required to elicit the increases in sirtuin activity required to combat age-related diseases.

Figure 1:
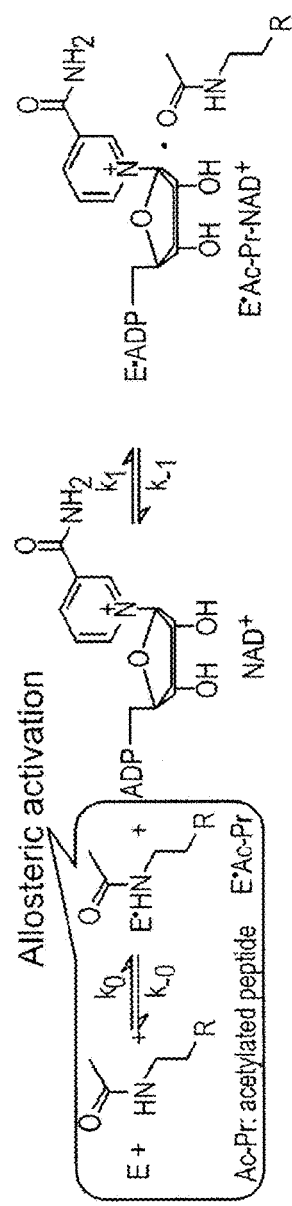
FIG. 1. Chemical mechanism of sirtuin-catalyzed deacylation and modes of sirtuin activation. Following sequential binding of acylated peptide substrate and NAD+ cofactor, the reaction proceeds in two consecutive stages: i) cleavage of the nicotinamide moiety of $NAD^+$ through the nucleophilic attack of the acetyl-Lys side chain of the protein substrate to form a positively charged O-alkylimidate intermediate, and ii) subsequent formation of deacylated peptide. Allosteric activation increases the affinity of selected peptide substrates for the SIRT1 enzyme and requires an allosteric binding site. Mechanism-based activation is a new mode of enzyme activation that relies on the conserved sirtuin reaction mechanism rather than an allosteric site.
Figure 1:
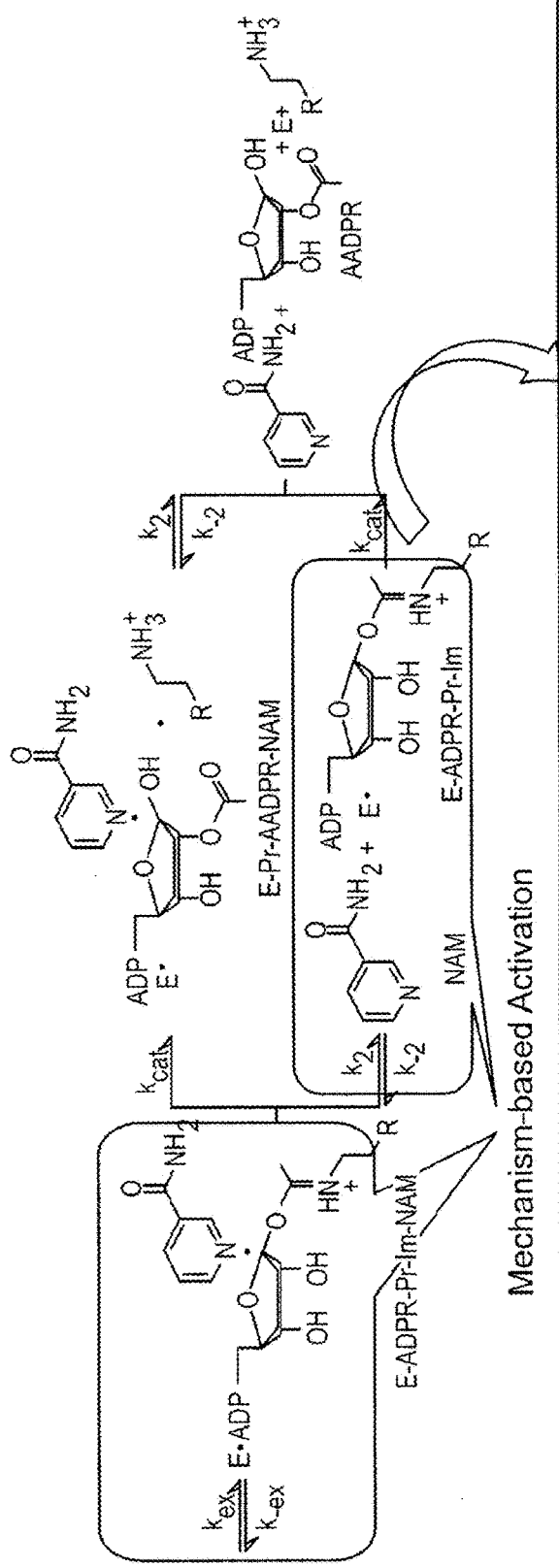
Figure 1:
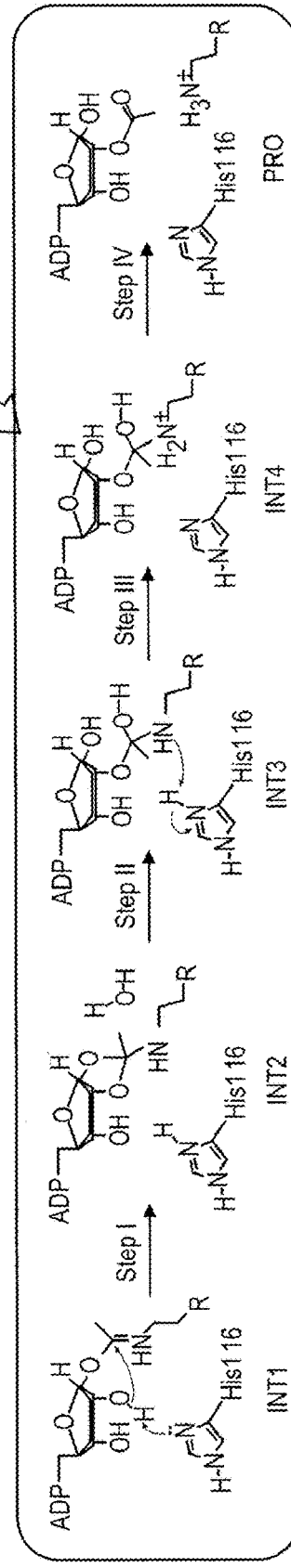

A preferred general strategy for activation of sirtuins (FIG. 1) would be to increase their sensitivity to NAD+ through a reduction of $K_{m,NAD+}$. $K_{m,NAD+}$ reduction would have a similar activating effect to NAD+ supplementation, but would be selective for sirtuins and could potentially even provide isoform specific sirtuin activation. Unlike allosteric activation, this approach would be applicable to any sirtuin and any substrate. Importantly, due to the sirtuin nicotinamide cleavage reaction that involves the NAD+ cofactor, modulation of $K_{m,NAD+}$ may in principle be achievable by means other than altering the binding affinity of NAD+ (FIG. 1).

Figure 4:
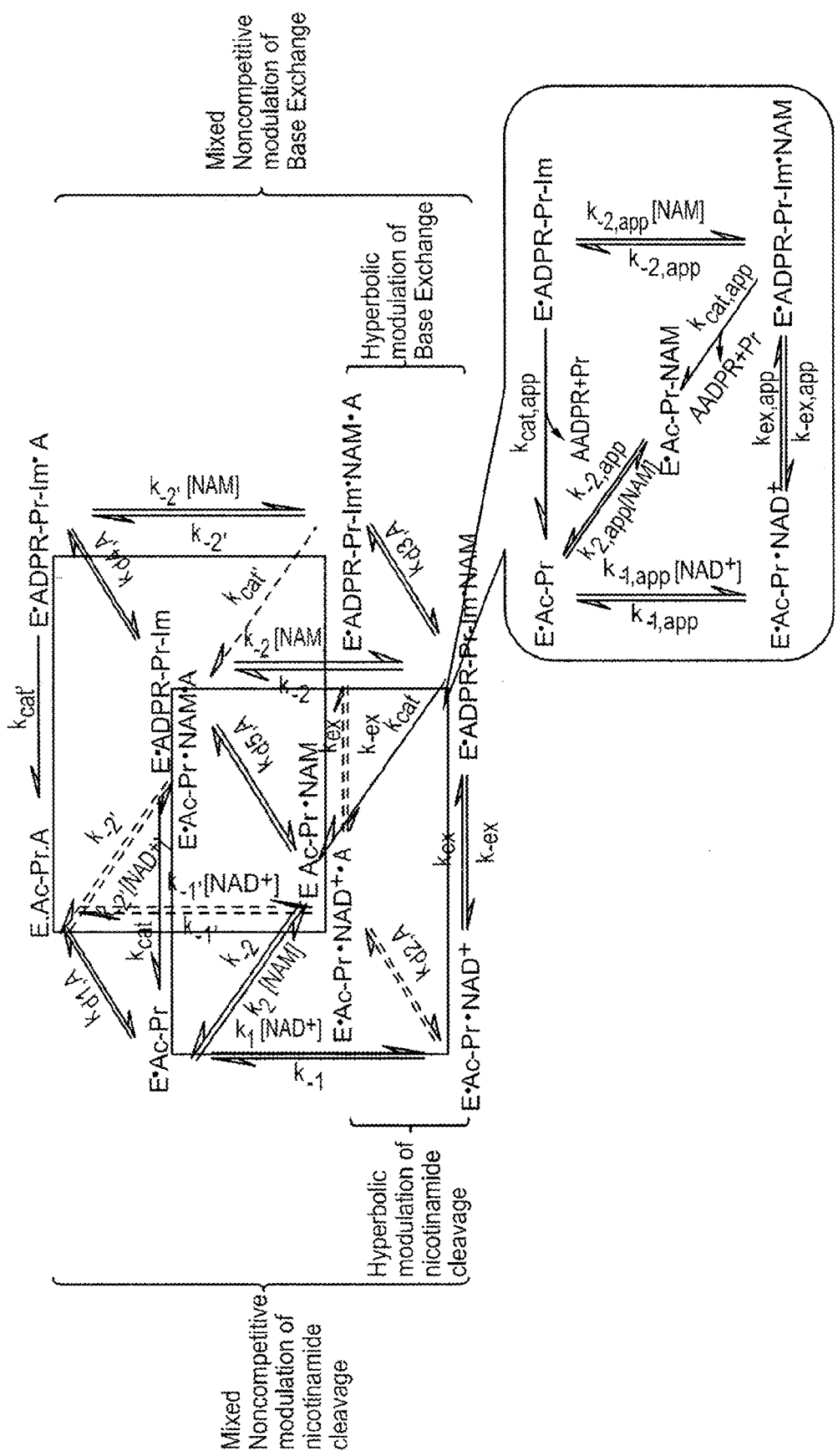
FIG. 4. General model for mechanism-based sirtuin enzyme activation. The front face of the cube depicts the salient steps of the sirtuin reaction network in the absence of bound modulator. The back face of the cube depicts the reaction network in the presence of bound modulator (denoted by "A"). Each rate constant depicted on the front face has an associated modulated value on the back face, designated with a prime that is a consequence of modulator binding. In the absence of modulator, the reaction proceeds solely on the front face; whereas in the presence of saturating concentration of modulator, the reaction proceeds solely on the back face. The projected face of the bottom rights is the apparent reaction network in the presence of a nonsaturating concentration of modulator. On this face, each rate constant is replaced by an apparent value, denoted by "app." Mixed noncompetitive modulation of nicotinamide cleavage and base exchange involves binding of A to the reaction species on the left and right sides of the front face, respectively, whereas hyperbolic modulation by A involves alteration of the rate constants for nicotinamide cleavage and base exchange ($k_{ex}$ and $k_{-ex}$, respectively). For small [A], the effect of the side and back faces of the cube on the apparent rate constants is modeled under a rapid equilibrium approximation, whereas a full steady state analysis is applied to the front face.

Based on the expression above for $K_{m,NAD+}$, it is in principle possible to activate sirtuins (not just SIRT1) by alteration of rate constants in the reaction mechanism other than $k_1, k_{-1}$ and $k_{cat}$, so as to reduce $K_{m,NAD+}$ (not $K_{d,Ac-Pr}$ as with allosteric activators, which increase the peptide binding affinity in a substrate-dependent fashion). In the instant invention, the kinetic model is augmented to include putative mechanism-based activators (A) that can bind simultaneously with NAD+ and NAM. FIG. 4 depicts the reaction diagram for mechanism-based activation of sirtuins. Note that only the top and front faces of this cube are relevant to the mechanism of action of the previously proposed competitive inhibitors of base exchange and deacylation.

At any [A], there exist apparent values of each of the rate constants in the sirtuin reaction mechanism. These are denoted by "app" in the Figure. There are also corresponding "app" values for each of the steady state, Michaelis, and dissociation constants. For characterization of a known activator, one can carry out complete steady state system identification at saturating [A], according to the methodology proposed above, to estimate the actual 7 back face rate constants in the presence of bound A (the rate constants designated by primes in the Figure). Moreover, at saturating [A] of a known activator, the modulated equilibrium and dissociation constants (which do not depend on determination of steady state species concentrations) can be estimated with only deacylation experiments according to the theory presented above.

Since the magnitudes of the $K_{d,A}$'s or binding affinities ($\Delta G_{bind}$) of A do not directly affect the shape of the dose response curves and the maximum level of activation, the ratios of $K_{d,A}$'s that appear in the equations above and hence the relative binding affinities of the front and back face complexes ($\Delta\Delta G_{bind}$'s) are the thermodynamic quantities of interest. Whereas this biophysical information, which can be estimated through steady-state deacylation experiments, is of significant interest for a known activator, it does not directly provide predictions for the effect on $K_{m,NAD+,app}$ of a modulator with specified relative binding affinities for the complexes in the sirtuin reaction mechanism—which is crucial to the mechanism of action of a potential activator. Therefore a model that is capable of predicting, under suitable approximations, the effect of a modulator with specified binding affinities on the apparent steady state parameters of the enzyme is important.

Since the full steady state expression relating the original to the apparent rate constants has many terms containing products of additional side and back face rate constants, in the instant invention, a simpler augmented kinetic model is used. A rapid equilibrium segments approach is used to arrive at simple definitions of the apparent Michaelis constant and other steady state constants for the reaction in terms of the original expressions for these constants and the dissociation constants for binding of A to the various complexes in the sirtuin reaction mechanism. This provides a minimal model with the least number of additional parameters required to model sirtuin activation mechanisms. It is assumed that rapid equilibrium applies on both the side faces and the back face. Traditional rapid equilibrium models of enzyme inhibition involve the binding events depicted on the side faces of FIG. 4 and, in some cases (hyperbolic inhibition) on the nicotinamide cleavage and exchange rate constants. However, as shown below, activation mechanisms for sirtuins may simultaneously involve both side faces and hence both $k_{ex}, k_{-ex}$ on the front face. Combination of these results in the introduction of $K_{ex}$ and $K_{ex}'$ in the activation model and requires a steady state treatment across the front face. This face and associated equilibrium constants do not arise in conventional models of enzyme inhibition.

The rapid equilibrium segments model is introduced in order to consider the plausibility and biophysical requirements of mechanism-based activation based only on the free energy changes of the various species in the sirtuin reaction mechanism upon binding A. This model assumes the changes in species concentrations in the presence of A are determined by the $K_{d,A}$'s and the dissociation and exchange constants on the back face in FIG. 4. Note that at high [A], this will not be the case—steady state modeling must be applied to the back face in that case in order to predict the concentrations of the various species and the associated apparent Michaelis constant ($K_{m,NAD+,app}$). Under this approximation, at low [A] it is assumed that the changes in each of the rate constant products in $c_{ij}$ and $c_{i',j'}$, $i'=i$, are the same and linear in [A]. Based on equation (1) and the aforementioned approximations, the rapid equilibrium segments expressions for the various steady-state species concentrations are as follows:

$$[E.Ac-Pr]/[E.Ac-Pr]_0 \approx c_{11} + c_{12}[NAM] \qquad (9)$$

$$[E.Ac-Pr.A]/[E.Ac-Pr]_0 \approx \frac{[A]}{K_{d1,A}}(c_{11} + c_{12}[NAM])$$

$$[E.Ac-Pr.NAD^+]/[E.Ac-Pr]_0 \approx c_{21}[NAD^+] + c_{22}[NAD^+][NAM]$$

$$[E.Ac-Pr.NAD^+.A]/[E.Ac-Pr]_0 \approx$$
$$\frac{[A]}{K_{d2,A}}(c_{21}[NAD^+] + c_{22}[NAD^+][NAM])$$

$$[E.ADPR-Ac-Im.NAM]/[E.Ac-Pr]_0 \approx$$
$$c_{31}[NAD^+] + c_{32}[NAD^+][NAM]$$

$$[E.ADPR-Ac-Im.NAM.A]/[E.Ac-Pr]_0 \approx$$
$$\frac{[A]}{K_{d3,A}}(c_{31}[NAD^+] + c_{32}[NAD^+][NAM])$$

$$[E.ADPR-Ac-Im]/[E.Ac-Pr]_0 \approx c_{41}[NAD^+]$$

$$[E.ADPR-Ac-Im.A]/[E.Ac-Pr]_0 \approx \frac{[A]}{K_{d4,A}}(c_{41}[NAD^+])$$

$$[E.Ac-Pr.NAM]/[E.Ac-Pr]_0 \approx$$
$$c_{51}[NAD^+] + c_{52}[NAM] + c_{53}[NAD^+][NAM]$$

$$[E.Ac-Pr.NAM.A]/[E.Ac-Pr]_0 \approx$$
$$\frac{[A]}{K_{d5,A}}(c_{51}[NAD^+] + c_{52}[NAM] + c_{53}[NAD^+][NAM])$$

Expressions for apparent values of all steady state parameters introduced above (i.e., modulated versions of constants $v_{max}, K_{m,NAD+}, K_1, K_2, K_3$) in the presence of a given [A] are derived. In the following, several types of approximations are invoked:

i: rapid equilibrium segments approximation ii: $k_{cat}(1+K_{dl,A}) \ll k_j(1+K_{dl',A})$, j≠cat, l=1, . . . , 5 iii: $k_{-2}(1+K_{dl,A}) \gg k_j(1+K_{dl',A})$, j≠-2, l=1, . . . , 5 (rapid NAM dissociation)

$\dfrac{v_{max,app}}{[E]_0}$: (10)

$$\frac{v_{max,app}}{[E]_0} = \frac{k_{cat,app}(c_{31,app} + c_{41,app})}{c_{21,app} + c_{31,app} + c_{41,app} + c_{51,app}}$$

$$\approx \frac{\begin{array}{c}k_{cat}(k_{cat}k_1 k_{ex} k_{-2}(1+[A]/K_{d3,A}) + \\ k_1 k_{ex} k_{-2} k_{-2}(1+[A]/K_{d4,A}))\end{array}}{\begin{array}{c}k_{cat}(k_{-2}k_1 k_{cat} + k_{-2}k_1 k_{-2} + k_{-2}k_1 k_{-ex})(1\,[A]/K_{d2,A}) + \\ k_{cat}k_1 k_{ex} k_2 (1+[A]/K_{d3,A}) + \\ k_1 k_{ex} k_{-2} k_{-2}(1+[A]/K_{d4,A}) + \\ k_{cat}k_1 k_{ex} k_{cat}(1+[A]/K_{d5,A})\end{array}}$$

$$\approx \frac{k_{cat} c_{41}(1+[A]/K_{dA,A})}{c_{41}(1+[A]/K_{dA,A})} = k_{cat}$$

$k_{cat,app} \approx k_{cat}$ $K_{m,NAD^+,app}$:

$$K_{m,NAD^+,app} = \frac{c_{11,app}}{c_{21,app} + c_{31,app} + c_{41,app} + c_{51,app}} \quad (11)$$

$$\approx \frac{c_{11}\left(1 + \dfrac{[A]}{K_{d1,A}}\right)}{c_{21}\left(1 + \dfrac{[A]}{K_{d1,A}}\right) + c_{31}\left(1 + \dfrac{[A]}{K_{d3,A}}\right) + c_{41}\left(1 + \dfrac{[A]}{K_{d4,A}}\right) + c_{51}\left(1 + \dfrac{[A]}{K_{d5,A}}\right)}$$

$$\approx k_{cat}\left(\frac{1}{k_1} + \frac{K_{d,NAD^+}}{k_{ex}}\right)\frac{1+[A]/K_{d1,A}}{1+[A]/K_{d4,A}} \approx k_{cat,app}\left(\frac{1}{k_1} + \frac{k_{d,NAD^+,app}}{k_{ex}\dfrac{1+[A]/K_{d2,A}}{1+[A]/K_{d1,A}}}\right)\frac{1+[A]/K_{d1,A}}{1+[A]/K_{d4,A}}$$

$$\approx k_{cat,app}\left(\frac{1}{k_{1,app}} + \frac{K_{d,NAD^+,app}}{k_{ex,app}}\right)$$

where it is assumed $k_{-2} \ll k_j$, $j \neq -2$ based on viscosity measurements that suggest NAM dissociates rapidly following cleavage.

$\alpha_{app}$ and $\alpha_{app} K_{m,NAD^+,app}$:

Note that $\alpha$ provides an estimate of the ratio of the dissociation and Michaelis constants for NAD+.

$$\alpha_{app} \approx \frac{c_{12}(1+[A]/K_{d1,A}) + c_{52}(1+[A]/K_{d5,A})}{c_{22}(1+[A]/K_{d2,A}) + c_{32}(1+[A]/K_{d3,A}) +} \cdot \frac{1}{K_{m,NAD^+,app}} \quad (12)$$
$$c_{53}(1+[A]/K_{d5,A})$$

$$\approx \frac{K_{d,NAD^+}}{K_{m,NAD^+}} \cdot \frac{K_{ex}}{1+K_{ex}} \cdot \frac{(1+[A]/K_{d4,A})}{(1+[A]/K_{d2,A})} \approx \frac{K_{d,NAD^+,app}}{K_{m,NAD^+,app}} \cdot \frac{K_{ex,app}}{1+K_{ex,app}}$$

$$\alpha_{app} K_{m,NAD^+,app} \approx \quad (13)$$

$$K_{d,NAD^+} \cdot \frac{K_{ex}}{1+K_{ex}} \cdot \frac{(1+[A]/K_{d1,A})}{(1+[A]/K_{d2,A})} \approx K_{d,NAD^+,app} \cdot \frac{K_{ex,ap}}{1+K_{ex,app}}$$

The latter provides an estimate of $K_{d,NAD^+,app}$ if $K_{ex} \gg 1$, as it is believed to be for most sirtuins.

$K_{3,app}$:

$K_3$ isolates nicotinamide cleavage/base exchange-specific effects.

$$\frac{1}{K_{3,app}} \approx \frac{\begin{array}{c}c_{22}(1+[A]/K_{d2,A}) + c_{32}(1+[A]/K_{d3,A}) + \\ c_{53}(1+[A]/K_{d5,A})\end{array}}{\begin{array}{c}c_{21}(1+[A]/K_{d2,A}) + c_{31}(1+[A]/K_{d3,A}) + \\ c_{41}(1+[A]/K_{d4,A}) + c_{51}(1+[A]/K_{d5,A})\end{array}} \quad (14)$$

$$\approx \frac{1+K_{ex}}{K_{d,NAM}} \cdot \frac{(1+[A]/K_{d2,A})}{(1+[A]/K_{d4,A})} \approx \frac{1+K_{ex,app}}{K_{d,NAM,app}}$$

$K_{2,app}$:

$$\frac{1}{K_{2,app}} = \frac{c_{12,app} + c_{52,app}}{c_{11,app}} \approx \frac{c_{12}(1+[A]/K_{d1,A}) + c_{52}(1+[A]/K_{d5,A})}{c_{11}(1+[A]/K_{d1,A})} \quad (15)$$

$$\approx \frac{c_{12}(1+[A]/K_{d1,A})}{c_{11}(1+[A]/K_{d1,A})} = \frac{K_{d,NAD^+} K_{ex}}{K_{m,NAD^+} K_{d,NAM}} \approx \frac{K_{d,NAD^+,app} K_{ex,app}}{K_{m,NAD^+,app} K_{d,NAM,app}}$$

Regarding the quality of the approximations in this case, note from (15) and (3) that unlike any of the other steady-state parameters, the modulation $$\frac{1}{K_{2,app}} - \frac{1}{K_2}$$

induced by [A] is proportional to $k_{cat}$ under the rapid equilibrium segments approximation (first approximation above). Hence, if one is interested in estimating the sign of this modulation, the small $k_{cat}$ approximation (second approximation above) should not be applied. Also, under the rapid equilibrium segments approximation, $K_{2,app}$ is the only constant that relies on a ratio of two $c_{ij}$'s with i'=i, j'≠j, and hence the ratio of the same factor in [A]. The apparent values of rate constant products in the numerator and denominator above cannot be precisely equal and hence $K_{2,app}$ will have to change slightly from $K_2$.

$K_{1,app}$:

$$K_{1,app} = \frac{c_{32,app}}{c_{31,app} + c_{42,app}} \quad (16)$$

$$\approx \frac{k_1 k_{ex} k_2 k_{-2}(1+[A]/K_{d3,A})}{k_{cat} k_1 k_{ex} k_{-2}(1+[A]/K_{d3,A}) + k_1 k_{ex} k_{-2}(1+[A]/K_{d4,A})}$$

$$\approx K_{d,NAM} \frac{1+[A]/K_{d3,A}}{1+[A]/K_{d4,A}}$$

Thermodynamic conditions on A binding for mechanism-based sirtuin activation under the rapid equilibrium segments approximation, along with the expected changes in each of the steady state, equilibrium and dissociation constants in the sirtuin reaction mechanism, are presented below.

According to equation (10), $$\frac{v_{max,app}}{[E]_0}$$

is roughly unchanged within this family of mechanisms as long as the $K_{d,A}$'s for [A] binding to the various represented complexes in the reaction mechanism satisfy condition (iii). Thus, enzyme activation is expected if $K_{m,NAD^+,app}$ can be decreased relative to $K_{m,NAD^+}$—i.e., by increasing the sensitivity of sirtuins to NAD+.

The analysis above enables the following choice of constraints on the ratios of parameters obtained from the assay in the presence of the test compound to the value in the absence of the test compound, in order for the test compound to qualify as a hit compound.

In one embodiment, a test compound is a hit compound if $v_{app}/v$ at a nonsaturating [NAD+]<$K_m$NAD+ exceeds a specified threshold value greater than 1.

In another embodiment, a test compound is a hit compound if the steady state parameters $v_{max,app}/v_{max}\approx 1$, and $K_{2,app}/K_2\approx 1$.

In another embodiment, a test compound is a hit compound if $K_{1,app}/K_1$ exceeds a specified threshold value greater than 1.

In another embodiment, the test compound is a hit compound if $K_{3,app}/K_3 > K_{2,app}/K_2$.

In another embodiment, the test compound is a hit compound if $$\frac{\alpha K_{m,NAD+}}{\alpha_{app} K_{m,NAD+,app}} \approx \frac{K_{d,NAD+}}{K_{d,NAD+,app}},$$

where the latter is determined by either the kinetic or binding affinity assay, exceeds a specified or predetermined threshold value. In some embodiments, for example, the specified or predetermined threshold value is generally less than 1.

In another embodiment, the test compound is a hit compound if $$\frac{K_{m,NAD+,app}}{K_{m,NAD+}} < \frac{\alpha_{app} K_{m,NAD+,app}}{\alpha K_{m,NAD+}} \approx \frac{K_{d,NAD+,app}}{K_{d,NAD+}}$$

where the latter is determined by either the kinetic or binding affinity assay.

Typically, a test compound is a hit compound if the net effect on catalytic turnover is activation ($v_{app}>v$). In some embodiments, even though the net effect on catalytic turnover is inhibition ($v_{app}<v$), a test compound can be a hit compound by its satisfaction of aforementioned ratios. For example, the net effect on catalytic turnover is inhibition and the net inhibitory effect is associated with the compound decreasing $$1/K_3 \approx \frac{1+K_{ex}}{K_{d,NAM}}$$

but increasing $K_{m,NAD^+}$, due to a concurrent increase in $K_{d,NAD^+}$.

In one embodiment, the effects of the hit compound at concentration [A] on steady state kinetic parameters $v_{max}$, $K_{m,NAD+}$, $K_1$, $K_2$, $K_3$, and $\alpha$ can be approximated as follows:

$$v_{max,app} \approx v_{max}$$

$$K_{m,NAD^+,app} \approx K_{m,NAD^+} \frac{1+[A]/K_{d1,A}}{1+[A]/K_{d4,A}}$$

$$\alpha_{app} \approx \frac{K_{d,NAD+}}{K_{m,NAD+}} \frac{K_{ex}}{1+K_{ex}} \frac{(1+[A]/K_{d4,A})}{(1+[A]/K_{d2,A})}$$

$$\frac{1}{K_{3,app}} \approx \frac{1+K_{ex}}{K_{d,NAM}} \frac{(1+[A]/K_{d2,A})}{(1+[A]/K_{d4,A})}$$

$$\frac{1}{K_{2,app}} \approx \frac{K_{m,NAD+} K_{d,NAM}}{K_{d,NAD+} K_{ex}}$$

$$\frac{1}{K_{1,app}} \approx K_{d,NAM} \frac{1+[A]/K_{d3,A}}{1+[A]/K_{d4,A}}$$

for defined values of $\frac{K_{d2,A}}{K_{d1,A}}; \frac{K_{d3,A}}{K_{d2,A}}$ and $\frac{K_{d4,A}}{K_{d3,A}}$.

Defined values of $$\frac{K_{d2,A}}{K_{d1,A}}; \frac{K_{d3,A}}{K_{d2,A}}; \frac{K_{d4,A}}{K_{d3,A}}$$

can be determined for a hit compound by thermodynamic parameters of the sirtuin-catalyzed deacylation in the presence of saturating concentrations of the hit compound, as follows:

$$\frac{K_{d2,A}}{K_{d1,A}} = \frac{K'_{d,NAD+}}{K_{d,NAD+}} \approx \frac{\alpha' K'_{m,NAD+}}{\alpha K_{m,NAD+}}; \frac{K_{d3,A}}{K_{d2,A}} = \frac{K'_{ex}}{K_{ex}}; \frac{K_{d3,A}}{K_{d4,A}} = \frac{K'_{d,NAM}}{K_{d,NAM}}$$

wherein $K_{d,NAM}'$, $\alpha'$, $K_{m,NAD+}'$, $K_{ex}'$ and $K_{d,NAM}$, $\alpha$, $K_{m,NAD+}$, $K_{ex}$ are determined according to the aforementioned methods applied at saturating concentrations of the hit compound and in the absence of the hit compound, respectively.

On the other hand, a test compound that does not satisfy assumptions (i-iii) would be screened out based on its uncharacteristic initial rate behavior, which will not fit the mechanism-based modulation model (for example, by failing to bind to all four relevant species in the reaction mechanism).

For example, prior attempts at non-allosteric sirtuin activation considered the use of competitive inhibitors of base exchange (like isonicotinamide, isoNAM) to activate sirtuins at nonzero [NAM]. Aside from allosteric activation, this is the only other previously proposed mode of sirtuin enzyme activation that has been experimentally investigated. These modulators rely on a favorable balance between competitive inhibition of base exchange and deacylation for activation. Importantly, this approach cannot reduce $K_{m,NAD+}$. At [NAM]=0, it will always increase the apparent value of $K_{m,NAD+}$. Competitive inhibition of base exchange can only reduce the $K_{m,NAD+,app}$ at nonzero [NAM] in eqn (1). As such, this is not actually a form of enzyme activation, despite the informal use of the term, but rather derepression of inhibition.

Figure 11:
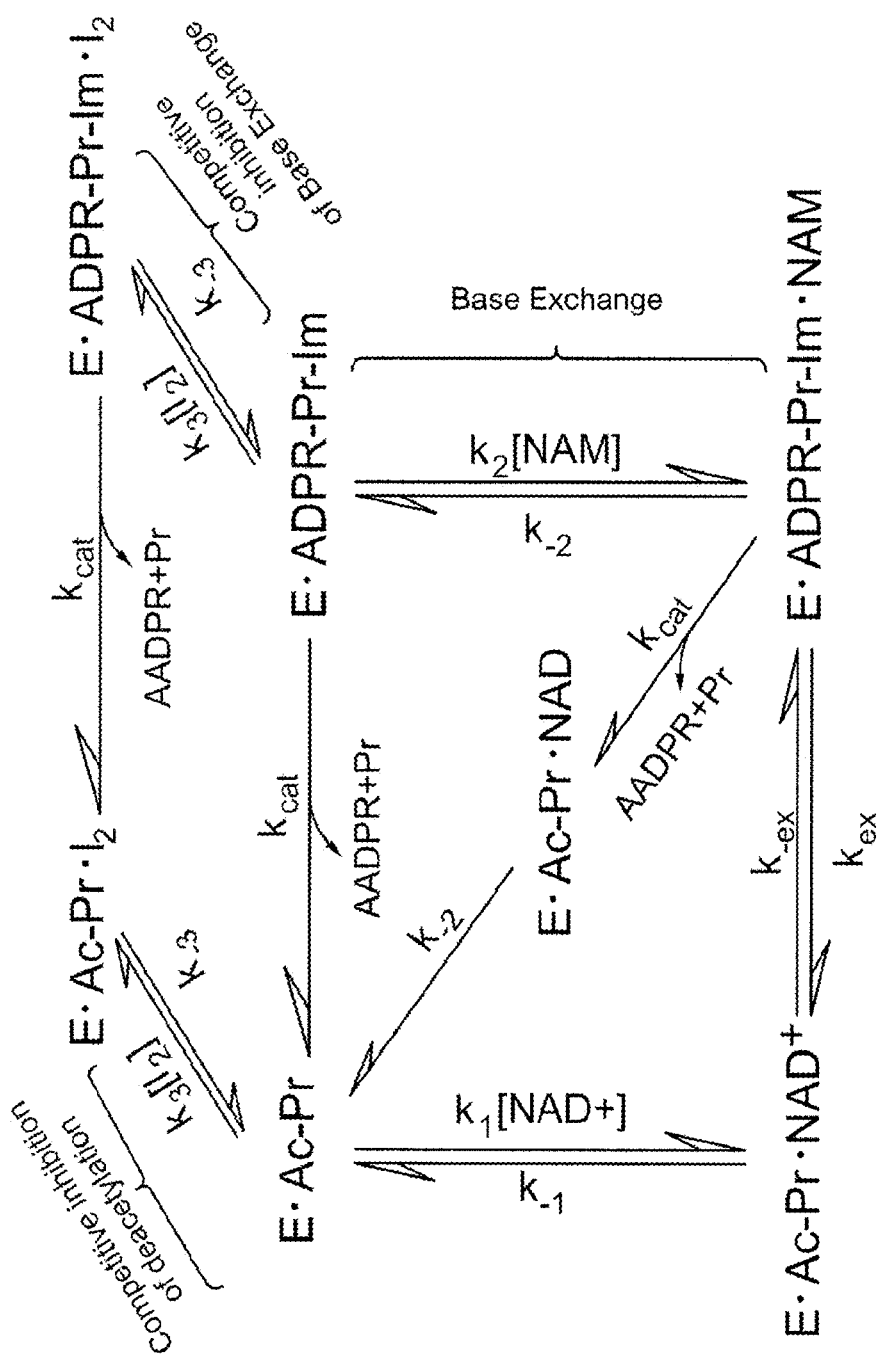
FIG. 11. Reaction network for derepression of base exchange inhibition. $I_2$ denotes a ligand that binds to both intermediate E.ADPR-Pr-Im and E.Ac-Pr. Compare FIG. 2. Note that the representation above corresponds to the simplification where Ac-Pr is present in saturating concentrations and E can hence be omitted from the network.

The basic kinetic model presented in equations (1), (3), and (5) is essential for quantitative analysis of such NAM derepression modalities, with previously reported formulations being approximations. An extended steady state model including the small molecule modulator is required for proper analysis, given that the modulator competes with NAD+ and NAM to form new species rather than preferentially stabilizing certain species in the deacylation reaction mechanism. See FIG. 11. To summarize the salient results, competitive inhibitors of base exchange will simultaneously increase $K_{d,NAD+,app}$ to an extent that depends on the sirtuin's value of $\alpha$. The greater the value of $\alpha$ for a sirtuin enzyme, the greater the increase in $K_{d,NAD+,app}$ that accompanies a given reduction in base exchange inhibition. This means that for most sirtuins, a competitive inhibitor of base exchange will display a significant extent of competitive inhibition of deacylation, at concentrations required for rate enhancement. This will reduce the maximum possible extent of rate enhancement.

Note that for competitive inhibition of base exchange like isoNAM, unlike the noncompetitive modulation modes depicted in FIG. 4, interpretation of the apparent steady state constants in terms of the apparent dissociation and exchange constants of the sirtuin reaction mechanism is no longer valid since approximation (ii) above does not hold.

Thus, such derepression modalities do not fit the definition of mechanism-based sirtuin enzyme activation.

In one embodiment, a test compound is "screened out" as not being a hit compound if, at concentration [A], the test compound does not satisfy the following relations:

$$v_{max,app} \approx v_{max}$$

$$K_{m,NAD+,app} \approx K_{m,NAD+} \frac{1 + [A]/K_{d1,A}}{1 + [A]/K_{d4,A}}$$

$$\alpha_{app} \approx \frac{K_{d,NAD+}}{K_{m,NAD+}} \frac{K_{ex}}{1 + K_{ex}}$$

$$\frac{1}{K_{3,app}} \approx \frac{1 + K_{ex}}{K_{d,NAM}} \frac{(1 + [A]/K_{d2,A})}{(1 + [A]/K_{d4,A})}$$

$$\frac{1}{K_{2,app}} \approx \frac{K_{m,NAD+} K_{d,NAM}}{K_{d,NAD+} K_{ex}}$$

$$\frac{1}{K_{1,app}} \approx \frac{1}{K_{d,NAM}} \frac{1 + [A]/K_{d3,A}}{1 + [A]/K_{d4,A}}$$

for some values of $\frac{K_{d2,A}}{K_{d1,A}}; \frac{K_{d3,A}}{K_{d2,A}}$ and $\frac{K_{d4,A}}{K_{d3,A}}$.

In one embodiment, a test compound is "screened out" as not being a hit compound if $\alpha_{app} * K_{m,NAD+,app} \ll K_{d,NAD+} \approx \alpha * K_{m,NAD+}$.

Validation of a Hit Compound

The high-throughput kinetic assays applied in the hit identification step may identify false positive hits. In hit validation, label- and reporter-free kinetic assays are used to repeat the kinetic assays from hit identification, and more rigorous measurements of binding affinities of ligands in the catalytic mechanism of the enzyme are carried out with unreactive substrate and intermediate analogs. The latter include measurement of the binding affinities of: i) an unreactive NAD analog to the complex of enzyme with acylated peptide and the hit compound, ii) NAM to the complex of enzyme with an unreactive alkylimidate intermediate analog and the hit compound, iii) O-acylated ADP ribose (O-AADPR) to the complex of enzyme with deacylated peptide and the hit compound.

A hit compound is validated if the ratios of specified steady state or equilibrium constants in the presence/absence of the hit compound determined hereinabove exceed certain specified or predetermined values.

In one embodiment, the hit compound is validated if the conditions satisfied by the hit compound in the hit identification step are also satisfied using the label- and reporter-free assay.

In one embodiment, the hit compound is validated if $K_{d,NAM,app}/K_{d,NAM}$, determined using either the kinetic or binding affinity assays, exceeds a threshold value, the threshold value being greater than 1.

In one embodiment, the hit compound is validated if $K_{d,NAD+}/K_{d,NAD+,app}$, determined using either the kinetic or binding affinity assays, exceeds a threshold value, the threshold value being less than 1.

In one embodiment, the hit compound is validated if $K_{d,OAADPR,app}/K_{d,OAADPR}$, determined through either the kinetic or binding affinity assay, exceeds a threshold value, the threshold value being less than 1.

In one embodiment, the binding affinity is determined by isothermal calorimetry or microscale thermophoresis.

In one embodiment, the label-free kinetic assay is carried out using high-throughput liquid chromatography or mass spectrometry.

In one embodiment, the unreactive NAD analog is carba-NAD (carbanicotinamide adenine dinucleotide) and the unreactive alkylimidate intermediate analog is thioalkylimidate intermediate.

In one embodiment of the instant invention, a hit compound is validated as a MB-STAC by a method comprising a cell-based assay for pharmacokinetic and cell toxicity characteristics of the hit compound through analysis of its absorption, distribution, metabolism and excretion (ADME) properties, wherein the hit compound is validated if each of these properties exceeds a specified threshold value.

Hit Evolution

In order to establish the additional properties that a hit compound must have in order to qualify as a MB-STAC lead compound, thermodynamic conditions on A binding for mechanism-based sirtuin activation under the rapid equilibrium segments approximation are considered, along with the expected changes in each of the steady state, equilibrium and dissociation constants in the sirtuin reaction mechanism. Lead compounds for MB-STACs should satisfy these conditions.

According to equation (11), $K_{m,NAD^+,app}$ will be smaller than $K_{m,NAD^+}$ if $$\frac{K_{d1,A}}{K_{d4,A}} \geq \frac{K_{d1,A}}{K_{d2,A}} \frac{K_{d2,A}}{K_{d3,A}} \frac{K_{d3,A}}{K_{d4,A}} > 1.$$

To identify mechanisms by which this can occur in terms of the steps in the sirtuin-catalyzed reaction, each of these three respective ratios of $K_{d,A}$'s are considered (or equivalently, the $\Delta\Delta G$'s of the NAD+ binding, exchange, and NAM binding reactions as indicated by equation (8)) induced by A binding.

According to equation (13), $K_{d1,A}/K_{d2,A} < 1$ would imply that A binding increases the binding affinity of NAD+ to the E.Ac-Pr complex. This is biophysically implausible for mechanism-based activation when dissociation constants for substrates decrease upon small molecule binding; this typically occurs through an allosteric mechanism. Thus, it is assumed that for a mechanism-based activator, $K_{d1,A} \geq K_{d2,A}$. Hence in order to have $K_{m,NAD^+,app} < K_{m,NAD^+}$, require $$\frac{K_{d2,A}}{K_{d3,A}} \frac{K_{d3,A}}{K_{d4,A}} > \frac{K_{d1,A}}{K_{d2,A}}$$

or equivalently, $$\frac{K'_{d,NAM}}{K'_{ex}} \frac{K_{ex}}{K_{d,NAM}} > \frac{K'_{d,NAD+}}{K_{d,NAD+}}.$$

The decrease in $K_{m,NAD^+}$ can be due to modulation of the exchange rate constants that induces a decrease in $K_{ex}$, an increase in $K_{d,NAM}$, or both. It is assumed that $K_{d,NAM}' \geq K_{d,NAM}$ ($K_{d3,A} > K_{d4,A}$) for reasons analogous to those for $K_{d,NAD^+}$ (NAM being the nicotinamide moiety of NAD+). This corresponds to mixed noncompetitive inhibition of base exchange, as depicted in FIG. 4.

As previously shown, the nicotinamide moiety of NAD+ engages in nearly identical interactions with the enzyme before and after bond cleavage. The salient difference is a conformational change in a conserved phenylalanine side chain that destabilizes NAM binding after bond cleavage.

Since NAM binding is already destabilized by the native protein conformation, and since $\Delta\Delta G_{bind,NAD+}$ induced by the modulator will generally be greater in magnitude than $\Delta\Delta G_{bind,NAM}$ due to disruption of additional contacts between the ADPR moiety of NAD+ and the enzyme, $$\frac{K_{d2,A}}{K_{d3,A}}$$

is likely to make the dominant contribution to $$\frac{K_{d2,A}}{K_{d4,A}}.$$

Note that there is ample scope for modulation of $\Delta G_{ex}$ by the modulator due to the coupling of the endothermic nicotinamide cleavage/ADP ribosylation reaction (exothermic base exchange reaction) to a conformational change in the sirtuin cofactor binding loop. $\Delta G_{ex}$ of immediate product formation for Sir2Tm has been calculated to be −4.98 kcal/mol. For comparison, $\Delta G_{bind,NAM}$ for Sir2Af2 was estimated to be −4.1 kcal/mol and $\Delta G_{bind,NAM}$ for SIRT3 was estimated to be $\leq$ −3.2 kcal/mol. Taken together, these observations suggest that $$\frac{K_{d2,A}}{K_{d3,A}} \gg \frac{K_{d3,A}}{K_{d4,A}}$$

and that the value of $$\frac{K_{d2}}{K_{d4}}$$

required for activation is likely to be achieved primarily by altering the free energy change of the nicotinamide cleavage reaction. However, the instant model accommodates the possibility of arbitrary combinations of $\Delta\Delta G_{ex}$ and $\Delta\Delta G_{bind,NAM}$ contributing to activation.

The following thermodynamic conditions on the binding of A to the various complexes in the sirtuin reaction mechanism are conducive to mechanism-based activation:

$$K_{d1,A} \leq K_{d2,A} \Leftrightarrow K'_{d,NAD+} \geq K_{d,NAD+} \quad (17)$$

$$K_{d2,A} \gg K_{d3,A} \Leftrightarrow K_{ex} \ll K'_{ex},$$

$$K_{d3,A} \geq K_{d4,A} \Leftrightarrow K'_{d,NAM} \geq K_{d,NAM}$$

where the $\gg$ sign signifies that $\frac{K_{d2,A}}{K_{d3,A}} > \frac{K_{d3,A}}{K_{d4,A}}$.

It is assumed that both $K_{d,NAM}$'s in FIG. 4—namely, those for dissociation of NAM from E.Ac-Pr.NAM and E.ADPR-Pr-Im.NAM—are roughly equal (given that A is assumed to not interact directly with the peptide of ADPR moiety, and since NAM binding does not rely on interactions with the flexible cofactor binding loop). Hence:

$$\frac{[E.ADPR - Pr - Im][NAM]}{[E.ADPR - Pr - Im.NAM]} \approx \frac{[E.Ac - Pr][NAM]}{[E.Ac - Pr.NAM]} \Leftrightarrow \quad (18)$$

$$K_{d5,A} \approx \frac{K_{d1,A} K_{d3,A}}{K_{d4,A}}$$

Returning to equation (11) for $K_{m,NAD^+,app}$ and substituting $$\frac{1+[A]/K_{d2,A}}{1+[A]/K_{d1,A}} \geq 1,$$

the rapid equilibrium assumptions applied to the present system imply that in order to activate the enzyme at [NAM]= 0, A must increase $k_1$ ($k_{1,app} > k_1$), $k_{ex}$ ($k_{ex,app} > k_{ex}$) or both (the rapid equilibrium segments model is not able to distinguish between these scenarios). Given that A is prone to increase $K_{d,NAD^+,app}$ assuming that it also increases $k_1$ is physically implausible.

An increase in $k_{ex}$ implies acceleration of the rate of nicotinamide cleavage. In the rapid equilibrium segments framework, this occurs through preferential stabilization of the E.ADPR-Pr-Im complex. The biophysical underpinnings whereby such an increase in a forward rate constant could be achieved through stabilization of the intermediate complex are discussed below.

Considered below are the effects of A binding that satisfies the above requirements for activation on the remaining steady state constants.

- $\alpha_{app}$: According to equation (12), the aforementioned requirement for activation that $$\frac{K_{d2,A}}{K_{d4,A}} \geq \frac{K_{d1,A}}{K_{d4,A}}$$

implies a significant increase in $\alpha$ by a factor that will generally exceed $$\frac{K_{m,NAD+}}{K_{m,NAD+,app}}.$$

$K_{3,app}$: According to equation (14), in the presence of such a mechanism-based activator, $K_3$ is expected to increase by a factor similar to that for $\alpha$ under the rapid equilibrium segments approximation. This can occur due to an increase $K_{m,NAD,app}$ or decrease $K_{ex}$ or both. Decrease in $K_{ex}$ corresponds to hyperbolic noncompetitive inhibition of base exchange/activation of nicotinamide cleavage. With an additional increase in $K_{d,NAM}$, noncompetitive inhibition of base exchange becomes mixed noncompetitive inhibition of base exchange (FIG. 4).

Additional information (e.g., from high [NAM] initial rate experiments), which permits estimation of $K_{d,NAD+,app}$) is required to separate these possible causes.

$K_{2,app}$: With conditions (17), equation (14) predicts a small increase in $K_2$ since $K_{d5,A} > K_{d1,A}$. $K_2$ increases to a smaller extent than $K_3$.

$K_{1,app}$: With conditions (17), equation (16) predicts an increase in $K_1$.

A hit compound of a MB-STAC may not always satisfy the above relations. For example, a molecule that decreases $$\frac{k_{ex}}{K_{d,NAM}} (\Delta G_{24})$$

but either increases or does not decrease $K_{m,NAD^+}$ at non-saturating concentrations, due to a concurrent increase in $K_{d,NAD^+}$ ($\Delta G_{12}$) or insufficient $k_{ex}$ enhancement, would be identified by the screen as a potential activator, and hence a hit compound, although it is an inhibitor. Moreover, further improvement of the properties above may be desirable. These properties may be improved by hit evolution methods to generate lead compounds, as follows.

In one aspect of the instant invention, a method for evolving a hit compound for a MB-STAC into a lead compound is provided. The method comprises a) generating a mutation to at least one functional group on the hit compound to form a mutated hit compound; b) obtaining steady state parameter estimates, as described above, for deacylation of a sirtuin enzyme in the presence of a specified concentration of the mutated hit compound; c) measuring the binding affinity of an unreactive NAD analog to the complex of enzyme with substrate peptide and the hit compound, the binding affinity of NAM to the complex of enzyme with unreactive alkylimidate intermediate analog and the hit compound, and the binding affinity of O-acylated ADP ribose (OAADPR) to the complex of enzyme with deacylated peptide and the hit compound; d) optionally, assaying the extent of deacylation of a substrate peptide in a whole cell environment in the presence of the mutated hit compound and/or assaying ADME properties of the mutated hit compound; e) applying an optimization algorithm to improve the biophysical and kinetic properties of the mutated hit compound by generating additional mutations to at least one functional group so to effect at least one of the following:

- decreasing $K_{m,NAD+,app}$ of the enzyme in the presence of a specified concentration of the mutated hit compound;
- decreasing $K_{d,NAD+,app}$ of the enzyme, determined using either the kinetic or binding affinity assay, in the presence of a specified concentration of the mutated hit compound;
- decreasing $K_{ex,app}$ of the enzyme in the presence of a specified concentration of the mutated hit compound;
- increasing $K_{d,NAM,app}$ of the enzyme, determined using either the kinetic or binding affinity assay, in the presence of a specified concentration of the mutated hit compound;
- increasing $K_{d,OAADPR,app}$ of the enzyme in the presence of a specified concentration of the mutated hit compound;
- improving pharmacokinetic (ADME) properties of the mutated hit compound;
- increasing extent of deacylation of a substrate peptide in a cellular environment in the presence of a specified concentration of the mutated hit compound.

Typically, steps (a)-(e) are repeated for a specified number of algorithmic iterations, wherein the number of iterations is greater than or equal to the number required for $K_{m,NAD+}/K_{m,NAD+,app}$ or $v_{app}/v$ at a particular [NAD+] to exceed specified values greater than one.

Next the mutated hit compound is assayed with the method as described above, but at saturating concentrations to determine the modulated values $k_1', k_{-1}', k_2', k_{-2}', k_{ex}', k_{-ex}', k_{cat}'$ and $$K'_{d,NAD+} = K_{d,NAD+}\frac{K_{d2,A}}{K_{d1,A}}; \quad K'_{ex} = K_{ex}\frac{K_{d3,A}}{K_{d2,A}}; \quad K'_{d,NAM} = K_{d,NAM}\frac{K_{d3,A}}{K_{d4,A}};$$

and

The extent of deacylation of the substrate peptide in a cellular environment in the presence of a specified concentration of the mutated hit compound is assayed. The mutated hit compound is a lead compound if $v_{max,app} \approx v_{max}$, $K_{m,NAD+}/K_{m,NAD+,app}$ exceeds a specified value greater than one, and the extent of deacylation of the substrate peptide in a cellular environment in the presence of the mutated hit compound exceeds that in the absence of the mutated hit compound.

In one embodiment, a mutation is generated by hit fragmentation to identify promising fragments or pharmacophores, fragment linking, fragment expansion, fragment assembly, (bio)isosteric replacement, and combinations thereof. In one embodiment, a mutation is generated by solid or solution phase parallel synthesis and high throughput purification.

In one embodiment, the extent of deacylation of a substrate peptide in a cellular environment is determined by an assay comprising: a) a cell-based model for the activity of a sirtuin enzyme using either in vitro cell culture or cell lysate; b) an electrochemical, chemiluminescent or fluorescent readout; and/or c) quantification of expression of a reporter gene that is regulated by the relevant sirtuin or, direct or indirect assay of acylation state of sirtuin deacylation substrates at specified concentrations of hit compound.

In one embodiment, the substrate peptide is tubulin and the assay measures tubulin destabilization upon deacylation. For example, the assay can measure tubulin destabilization with fluorescently labeled anti-tubulin antibodies.

In one embodiment, the substrate peptide is BubR1 and the assay measures BubR1 that is stabilized against degradation by deacylation.

In one embodiment, the ratios of dissociation constants for binding of the lead compound to the enzyme+peptide substrate complex, enzyme+peptide substrate+NAD+complex, enzyme+alkylimidate intermediate+NAM complex, and enzyme+alkylimidate complex, denoted by $K_{d1,A}$; $K_{d2,A}$; $K_{d3,A}$; and $K_{d4,A}$ respectively, satisfy the following relations:

$$\frac{K_{d1,A}}{K_{d2,A}} \leq 1 \Leftrightarrow \frac{K'_{d,NAD+}}{K_{d,NAD+}} \geq 1$$

$$\frac{K_{d2,A}}{K_{d3,A}} \gg 1 \Leftrightarrow \frac{K'_{ex}}{K_{ex}} \ll 1$$

$$\frac{K_{d3,A}}{K_{d4,A}} \geq 1 \Leftrightarrow \frac{K'_{d,NAM}}{K_{d,NAM}} \geq 1$$

wherein the $\gg$ sign signifies that $\frac{K_{d2,A}}{K_{d3,A}} > \frac{K_{d3,A}}{K_{d4,A}}$.

Figure 3A:
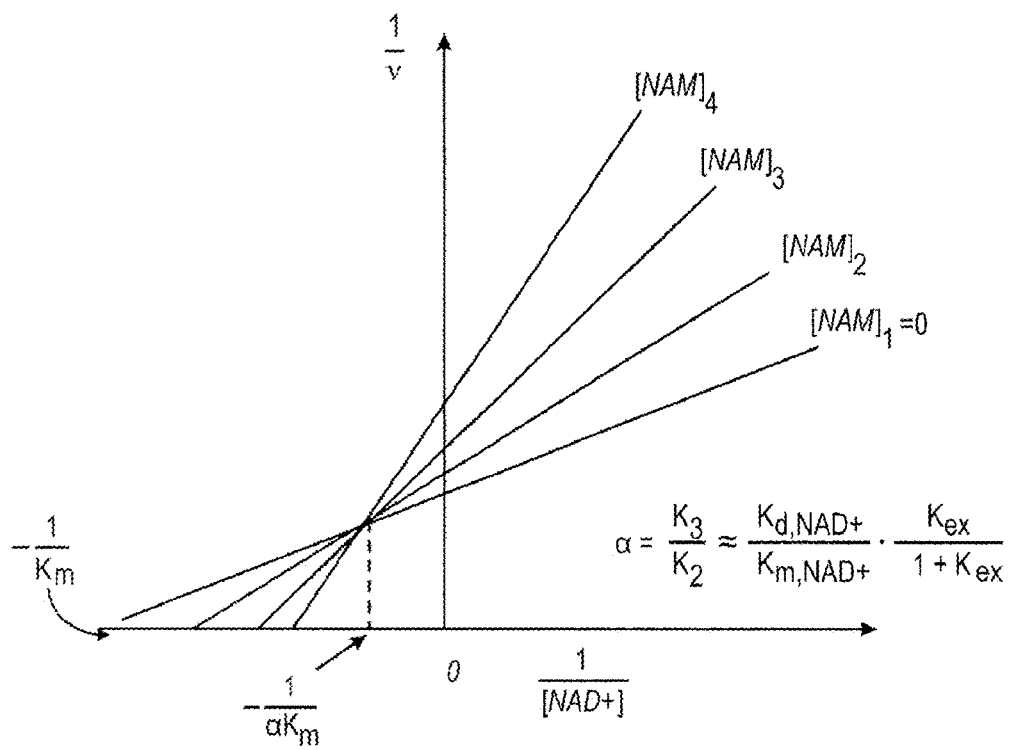
FIGS. 3A and 3B. Steady-state analysis of sirtuin-catalyzed deacylation in the presence of NAD+ and NAM: mechanistic interpretation.
Figure 3B:
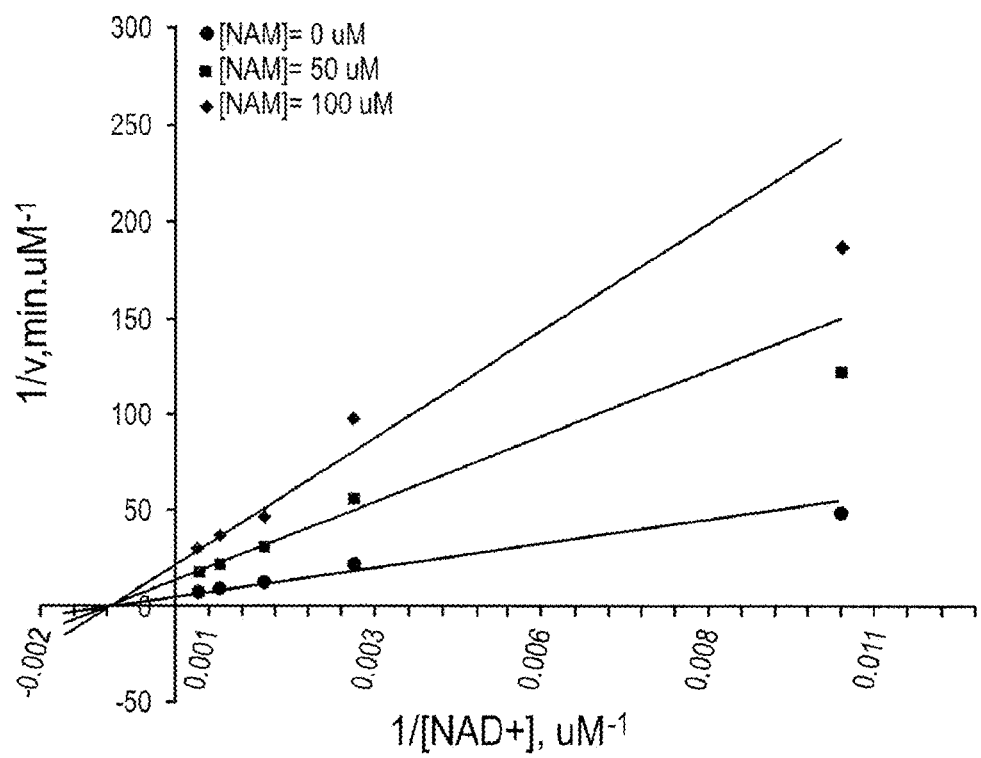

FIG. 5 depicts the model-predicted changes to the various steady state, Michaelis and dissociation constants in the sirtuin reaction mechanism in the presence of an MB-STAC lead compound. The subfigures demonstrate how varying [NAD+] and [NAM], respectively, provide complementary information required to elucidate the activator's mechanism of action. The double reciprocal plots in FIG. 5a pertain to the apparent face of FIG. 4 at $[A]=[A]_1$, whereas the double reciprocal plots at $[A]=0$ were depicted in FIG. 3. Note the change in the point of intersection (away from the x-axis) between FIG. 3a and FIG. 5a, due to the increase in the value of a predicted by equation (12). The Dixon plots in FIG. 5b show how variation of [NAM] provides information on the part of the apparent modulation effect that does not depend on $K_{d,NAD+}$. The slope of this plot at [NAM]=0 corresponds to $$\frac{K_{m,NAD+,app}}{v_{max,app}},$$

and hence the decrease in slope is due to the effect represented in property (11).

The property (14) of $K_{3,app}$ results in the slope of the Dixon plot $$\left(\frac{1}{K_{3,app}} \frac{1}{v_{max,app}}\right)$$

decreasing significantly at saturating [NAD+]. The significant change in slope of this plot indicates the primary cause of activation lies in the nicotinamide cleavage/exchange effect. The modulation depends only on $K_{ex}$ and $K_{d,NAM}$. Note that $K_{m,NAD+,app}$ also incorporates an NAM binding/dissociation effect, since the assumption of large $k_{-2}$ implies that the relevant free energy change for the nicotinamide cleavage reaction is that with respect to the intermediate without NAM bound. On the other hand, the reduction in the slope of the Dixon plot is less significant at lower [NAD+], due to property (15) of $K_{2,app}$.

Figure 5A:
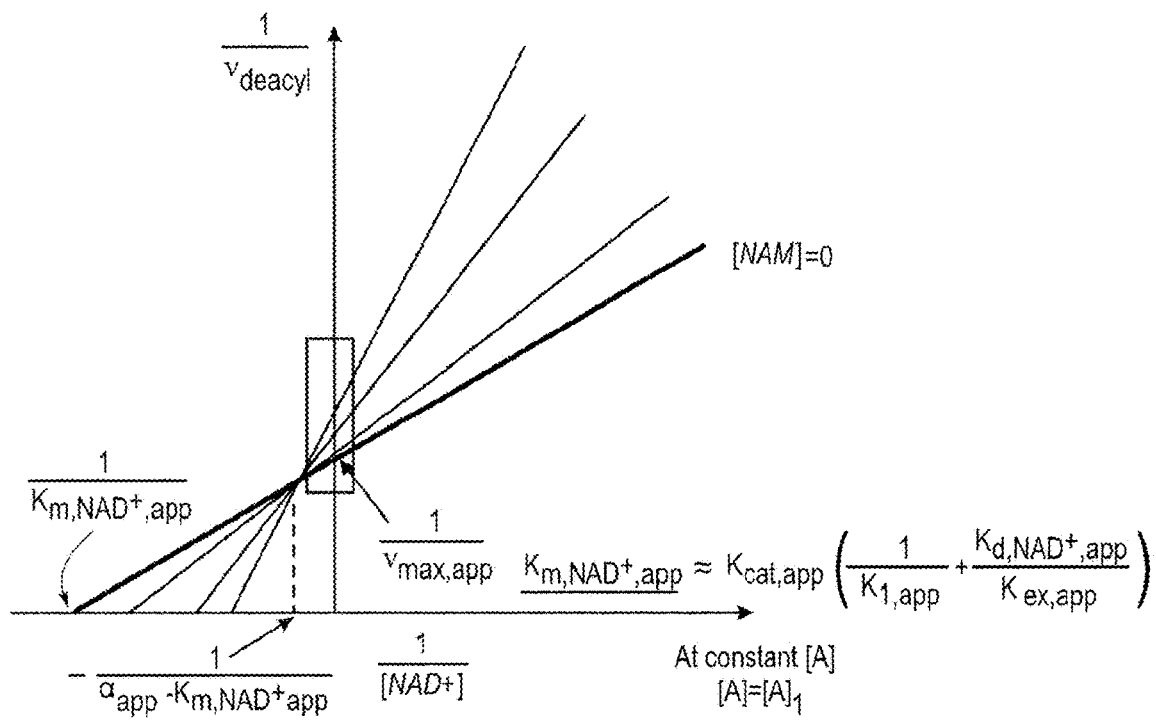
FIGS. 5A-5D. Mechanism-based activation of sirtuin enzymes: steady-state properties and dose-response behavior.
Figure 5B:
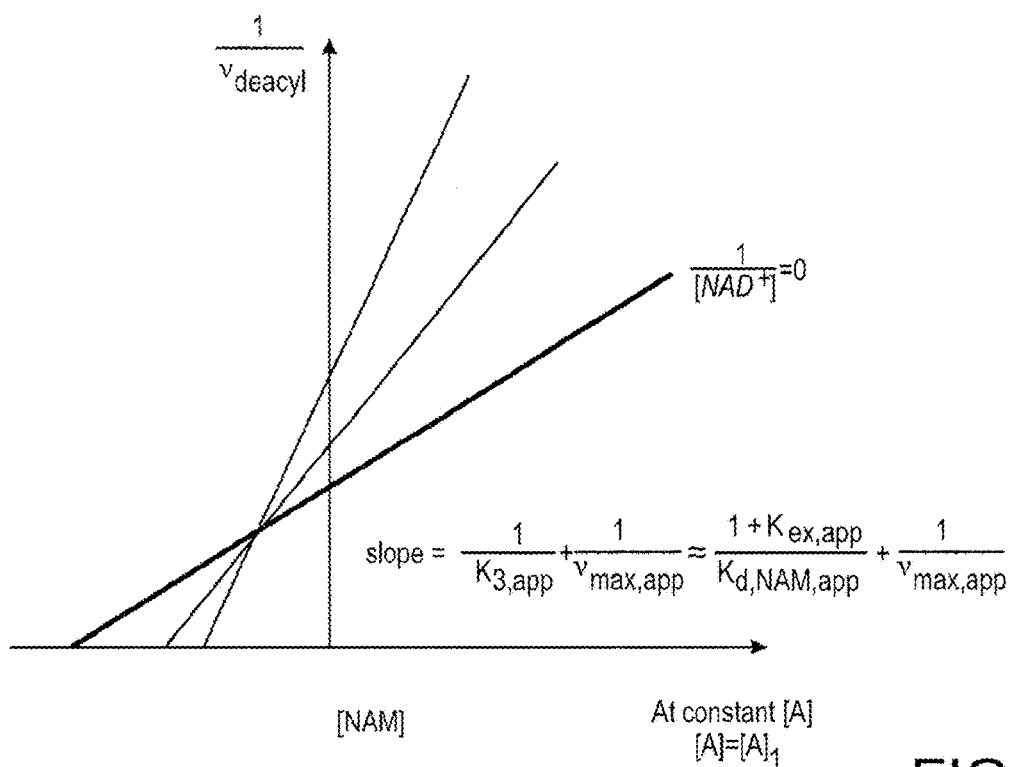
Figure 5C:
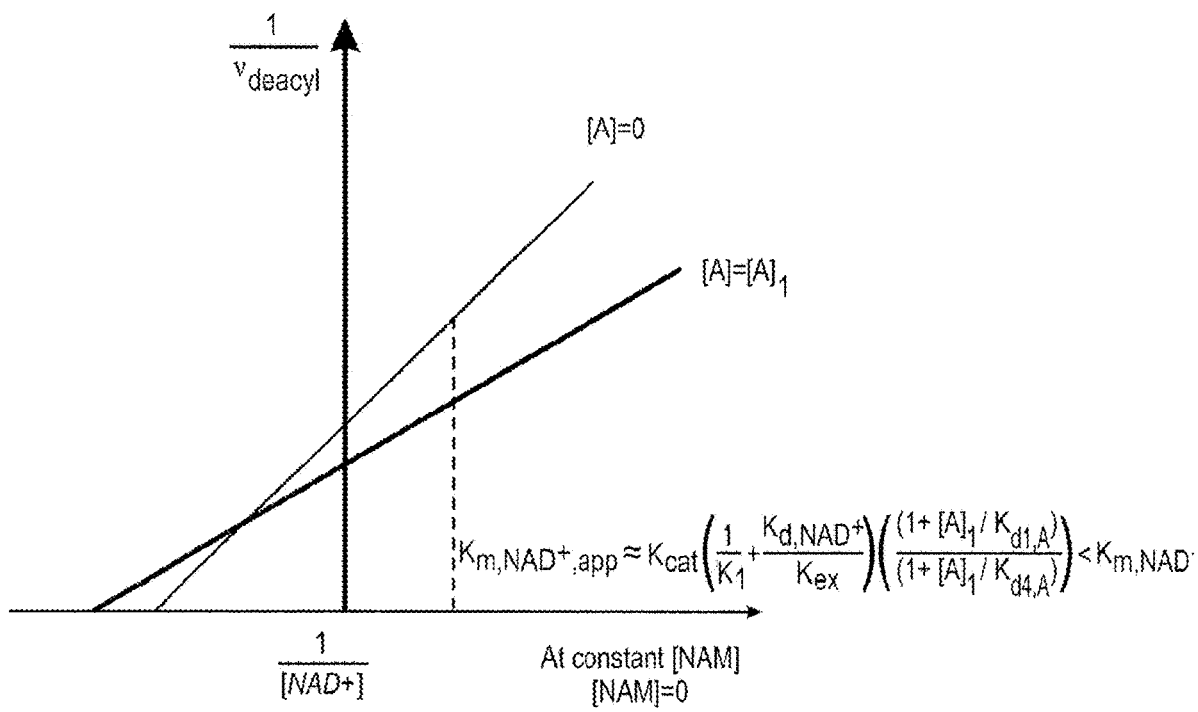
Figure 5D:
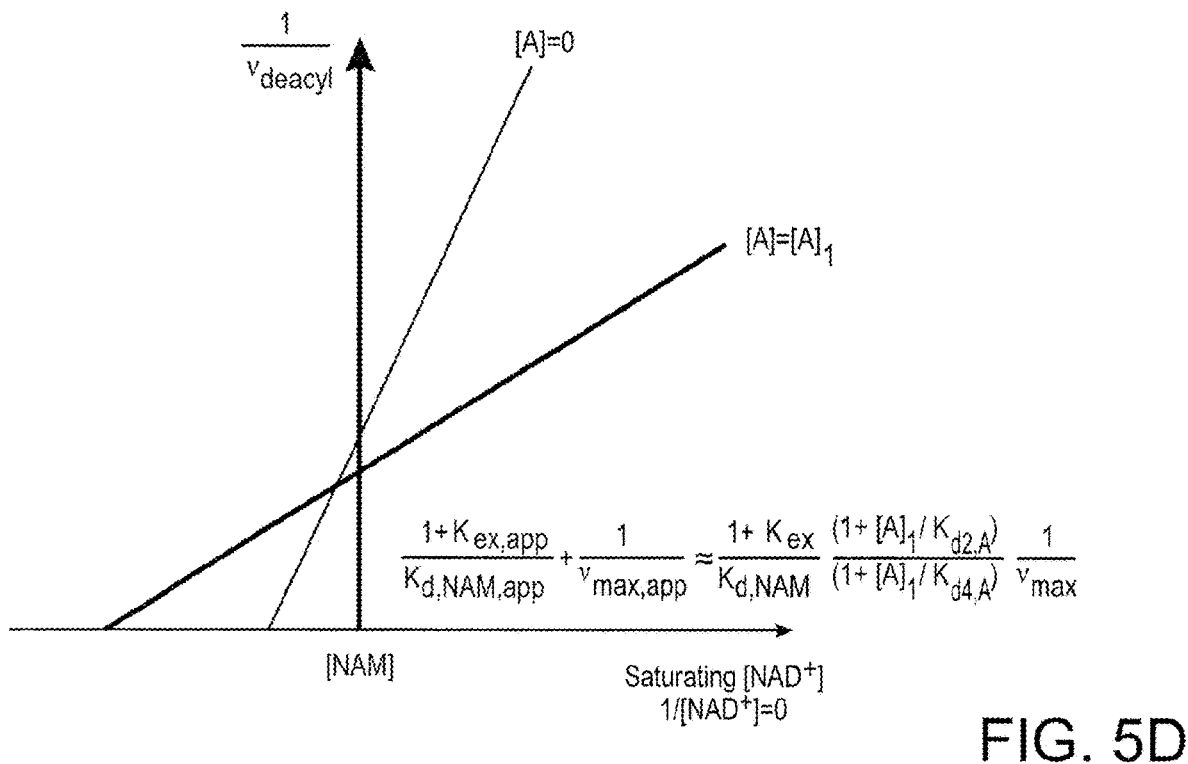

FIGS. 5c and d compare the expected double reciprocal and Dixon plots at [A]=0 and $[A]=[A]_1$, demonstrating how activation at [NAM]=0 relates to the differences in the characteristic features of these plots within the context of the rapid equilibrium segments model. The y-intercepts of FIG. 5c and d demonstrate the important feature that unlike allosteric activators, mechanism-based activators of the type described herein would not have a significant effect at saturating [NAD+], even at nonsaturating peptide substrate concentrations. This prediction can also be tested experimentally.

From the standpoint of chemical mechanisms of activation, the mechanism-based activation theory raises the important question of how the nicotinamide cleavage rate $k_{ex}$ of sirtuins can be accelerated by a ligand that binds to the various complexes in the deacylation reaction with the specified relative binding affinities, as predicted by equation (10), in terms of the transition states as well as reactant and product free energies. It is important to note in this regard that the nicotinamide cleavage reaction in sirtuins is generally believed to be endothermic (which enables effective NAM inhibition). Unlike exothermic reactions, stabilization of products in endothermic reactions can decrease the activation barrier for the forward reaction, due to the fact that the transition state resembles the products more than the reactants. This feature may also render a decrease in $K_{m,NAD+}$ for sirtuins more feasible than for many other classes of enzymes.

In one embodiment, the specified values of $v_{app}/v$ at a particular [NAD+] and $K_{m,NAD+}/K_{m,NAD+,app}$ are related by $$\frac{v_{app}}{v} = \frac{1 + \frac{[NAD^+]}{K_{m,NAD+}}}{\frac{K_{m,NAD+,app}}{K_{m,NAD+}} + \frac{[NAD^+]}{K_{m,NAD+}}}.$$

Figures 10A, 10B:
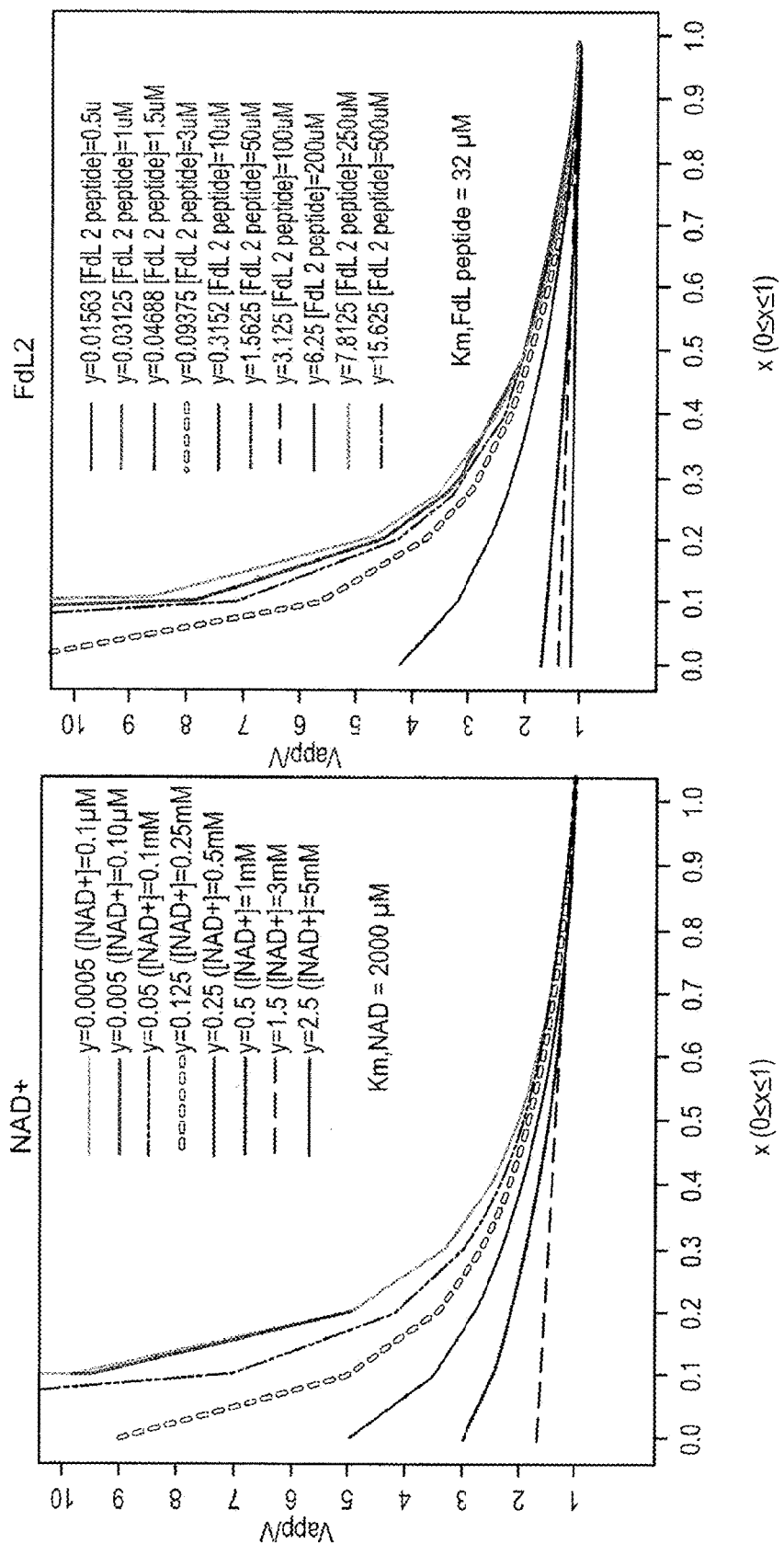
FIGS. 10A and 10B. Effect of $K_m$ reduction by a sirtuin activating compound on deacylation rate at specified values of substrate (NAD+, peptide) concentration as a fraction of $K_m$. The plots assume that $v_{max}$ is not altered by the compound.

This relation holds under the assumption that vmax is unchanged by the mutated hit compound. FIG. 10 depicts this relationship for various values of [NAD+].

Lead Optimization

In one aspect of the instant invention, a method for lead optimization of a mechanism-based sirtuin activating lead compound is provided. The lead compound can be obtained from the hit evolution method described above. The method comprises a) generating at least one mutation to at least one functional group on a lead compound to form a mutated lead compound; b) obtaining steady state parameter estimates, as described above, of a sirtuin enzyme in the presence of a specified concentration of the mutated lead compound; c) determining the binding affinity of the mutated lead compound to the enzyme+peptide substrate complex, enzyme+peptide substrate+unreactive NAD+ analog complex, enzyme+unreactive alkylimidate intermediate analog+NAM complex, and enzyme+unreactive alkylimidate analog complex; d) assaying at least one ADME property of the mutated lead compound; and accepting the mutation if either the binding affinity increases or an ADME property is improved, but $K_{m,NAD+app}$ obtained in (b) does not increase. Typically, steps (a)-(e) are repeated until the binding affinities in (c) and ADME properties in (d) exceed threshold values.

In one embodiment, the concentration of the mutated compound is a saturating concentration. In one embodiment, the mutation is generated by structure-based design. In one embodiment, the binding affinity is determined by isothermal calorimetry or microscale thermophoresis. In one embodiment, the unreactive NAD analog is carba-NAD (carbanicotinamide adenine dinucleotide) and the unreactive alkylimidate intermediate analog is thioalkylimidate intermediate.

In one embodiment, the optimization comprises minimizing the binding affinity of the lead compound for six sirtuins other than a target sirtuin, wherein the target sirtuin is one of SIRT 1-7.

EXAMPLES

The following examples serve to provide further appreciation of the invention but are not meant in any way to restrict the effective scope of the invention.

Chemicals and Reagents

The substrate peptides (including P53 derived peptides: QPKK-AMC and QPKK$^{Ac}$-AMC; and MnSOD derived peptide: KGELLEAIK$^{Ac}$RDFGSFDKF were synthesized at GenScript (Piscataway, N.J., USA) and PEPTIDE 2.0 Inc. (Chantilly, Va., USA). N-Benzyl-3,5-dicarboxy-4-phenyl-1,4-dihydropyridine (DHP-2) was synthesized at KareBay Biochem (Monmouth Junction, N.J., USA). All other chemicals used were of the highest purity commercially available and were purchased from Enzo Life Sciences (Farmingdale, N.Y., USA), Fisher Scientific (Pittsburgh, Pa., USA), Sigma (St. Louis, Mo., USA), and VWR (Radnor, Pa., USA).

Sirtuin Enzyme Expression and Purification

For the DHP-2 and Honokiol assays, human SIRT3 (102-399) plasmid with N-terminal fusion to a hexa-histidine affinity tag was purchased from OriGene. The protein was expressed in *E. coli* Arctic Express (DE3) cells (Agilent Technologies). A single colony was inoculated in 3 ml LB media containing 100 ug/ml ampicillin and 20 ug/ml gentamycin at 37° C., 250 rpm, overnight. The next morning, 200 ml LB medium, without any antibiotics was inoculated with 3 ml of the overnight culture and grown at 30° C., 250 rpm for 4 hours. The temperature was then lowered to 15° C. and the culture was allowed to equilibrate to the temperature for 30 min. Isopropyl 1-thio-D-galactopyranoside was added to a final concentration of 1 mM, and expression was continued at 15° C., 250 rpm for 24 hrs. Cells were collected by centrifugation, and the pellet was resuspended in buffer A1 (50 mM $NaH_2PO_4$, 300 mM NaCl, 20 mM imidazole, pH 8.0) and was sonicated to lyse the cells. Supernatant was separated from cell debris by centrifugation at 13.3×g for 30 min at 4° C. and loaded onto a 5 ml HisTrap HP column (GE Healthcare), pre-equilibrated with buffer A1 and attached to an AKTA pure FPLC system (GE Healthcare). The column was then washed with 10 column volumes of buffer A1, followed by 10 column volumes of buffer A2 (50 mM $NaH_2PO_4$, 300 mM NaCl, 75 mM imidazole, pH 8.0), followed by 10 column volumes of buffer A3 (20 mM Tris-HCl, 2M urea, pH 6.8), followed by 15 column volumes of buffer A2. The protein was eluted with buffer B1 (50 mM $NaH_2PO_4$, 300 mM NaCl, 300 mM imidazole, pH 8.0). The eluted protein was dialyzed against dialysis buffer (25 mM Tris, 100 mM NaCl, 5 mM DTT, 10% glycerol, pH 7.5) and concentrations were determined using the method of Bradford with bovine serum albumin (BSA) as the standard. All the above purification steps were performed at 4° C. The dialyzed protein was divided into several aliquots and stored in −80° C. until further use.

Hit Identification

Example 1

Figure 6C:
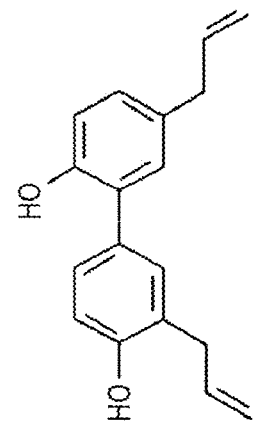
FIGS. 6A-6C. Sirtuin test compounds are illustrated.

The test compound in this example is N-Benzyl-3,5-dicarbethoxy-4-phenyl-1,4- dihydropyridine (DHP-1; FIG. 6A). Dihydropyridines (DHPs) constitute a class of compounds with drug-like properties that have been used to target calcium channels, among other proteins and associated disorders. The sirtuin is human SIRT3.

The specified concentration of the test compound was chosen to be 50 uM. Initial deacylation rates at DHP-1's were measured at varying [NAD+] and [NAM] according to the following methods.

High-throughput Initial Rate Measurements of Deacetylation Activity Using a Fluorolabeled Peptide The steady state parameters (Km and kcat) and catalytic efficiency (kcat/Km) of deacetylase activity of recombinant human SIRT3 were determined using a fluorimetric assay. The deacetylation activities were measured by using the SIRT3 Fluorimetric Drug Discovery Kit (AK 557, Enzo Life Sciences). This assay system allows detection of a fluorescent signal upon deacetylation of an acetylated substrate peptide, comprising amino acids 317-320 of human p53 (Gln-Pro-Lys-LysAc) for SIRT3, when treated with developer. The intensity of fluorescence was measured on a fluorometric microplate reader (Fluoroskan AscentH FL, Thermo Lab Systems) with excitation set at 355 nm and emission detection set at 460 nm. The initial rate of the $NAD^+$-dependent deacetylation activity of SIRT3 enzyme was measured at different concentrations of $NAD^+$. The reactions were carried out at 37° C. in a 50 µl reaction volume containing 50 mM Tris/Cl (pH=8), 137 mM NaCl, and 250 uM fluorolabeled peptide substrate. Reactions carried out in the presence of DHP-1 included 5% DMSO. The raw data were fitted to the Michaelis-Menten equation and defined inhibition models by using GraphPad Prism (GraphPad Software, Inc, CA) to obtain the kinetic constants. Fluorimetric assays of sirtuin activity have been shown to provide results comparable to those from assays using unmodified peptides in studies of nonallosteric modulators. In assays of allosteric modulators, artifacts reported in the presence of the fluorescent label were later shown to occur due to the hydrophobic fluorophore participating in the modulator's allosteric activation mechanism.

Measurement of the Effect of DHP-1 on SIRT3 Deacylation Activity

This assay was used to measure the potency of modulation of SIRT3 by DHP-1 in a high-throughput endpoint format. All reagents are diluted on ice in the following reaction buffer: 50 mM Tris/Cl, pH 8.0, 137 mM NaCl, 2.7 mM KCl, 1 mM MgCl$_2$, and 1 mg/mL BSA. Thus for each reaction well, 5U of SIRT3 enzyme is added to 500 µM NAD$^+$, 250 µM fluorolabeled peptide substrate, and DHP-1 at a given concentration (0-100 uM) in a total reaction volume of 50 µL. After an hour incubation at 37° C., the reaction is stopped upon addition of 1× Developer for a final reaction volume of 100 µL. The reaction is incubated at 37° C. for an additional 15 min and then read on the plate reader. Positive controls contained only enzyme, substrate, NAD$^+$, and DMSO while background controls contained substrate, NAD$^+$, and DMSO only.

Table 1 presents the results of model fitting to the initial rate data at 50 µM DHP-1 with the associated values of the initial rate parameters.

The mechanism of action of this modulator was investigated through initial rate analysis, which provides estimates for the apparent values of the steady state constants. The observed changes in the initial rate parameters $v_{max}$, $K_{m,NAD+}$, $\alpha$, $K_2$, $K_3$ in the presence of the activator were considered.

Based on the results of the fluorimetric assays, $v_{app} > v$ for DHP-1. It can be verified that based on the results of the fluorimetric assay, DHP-1 satisfies the specified constraints on the ratios of the apparent constants to their values in the absence of modulator that are required of a hit compound for an MB-STAC. In this example, the specified threshold value for $$\frac{\alpha K_{m,NAD+}}{\alpha_{app} K_{m,NAD+,app}} \approx \frac{K_{d,NAD+}}{K_{d,NAD+,app}}$$

is 1.5. Moreover, it can be verified that the modulator satisfies the relations for the effects of the hit compound at concentration [A] on steady state kinetic parameters $v_{max}$, $K_{m,NAD+}$, $K_1$, $K_2$, $K_3$, and $\alpha$, for some $K_{d2,A}$, $K_{d4,A}$ at [A]=50 uM. However, since high-throughput fluorimetric assays can generate false positives, validation of this hit is required.

TABLE 1

Model parameter estimates from global nonlinear fitting of mixed inhibition models for SIRT3 activation by DHP-1 in the presence of NAM, using a high-throughput labeled peptide initial rate assay. The values at 50 µM DHP-1 are apparent values. Note that the apparent activation observed using fluorolabeled peptide during the hit identification step was not validated during the hit validation step.

| Best-fit values | 0 uM DHP1c | 50 uM DHP1c |
|---|---|---|
| Vmax | 0.1911 | 0.2118 |
| Alpha | 1.139 | 1.933 |
| Ki | 29.81 | 36.93 |
| Km | 972.9 | 664.8 |
| Std. Error | | |
| Vmax | 0.006755 | 0.009142 |
| Alpha | 0.3519 | 0.8075 |
| Ki | 5.727 | 8.83 |
| Km | 85.04 | 82 |
| 95% Confidence Intervals | | |
| Vmax | 0.1762 to 0.2059 | 0.1917 to 0.2319 |
| Alpha | 0.3646 to 1.913 | 0.2105 to 3.765 |
| Ki | 17.20 to 42.42 | 17.50 to 56.37 |
| Km | 785.7 to 1160 | 484.3 to 8453 |
| Goodness of Fit | | |
| Degrees of Freedom | | |
| R square | 0.9948 | 0.9869 |
| Absolute Sum of Squares | 0.00004819 | 0.0001752 |
| Sy.x | 0.00259 | 0.004807 |

Example 2

In this example, the effect of Honokiol (FIG. 6C) on the binding affinity of NAD+ was assayed using microscale thermophoresis (MST).

Binding Analysis by Microscale Thermophoresis

Human Sirt3 protein was labeled with Alexa647 fluorophore by NHS ester chemistry in 20 mM HEPES, 200 mM NaCl, 0.5 mM TCEP at pH 7.5. A 2:1 molar excess of reactive dye was used over protein, in order to preferentially label one lysine within the protein. Free dye was removed using a size exclusion column and the labeled protein (Sirt3 NT647) was buffer exchanged into 50 mM Tris-HCl pH 8.0, 137 mM NaCl, 2.7 mM KCl, 1 mM MgCl2, 5% DMSO, 0.05% Pluronic F-127. A final concentration of 2 nM Sirt3 NT647 was titrated with varying concentrations of the modulator and thermophoresis was measured (excitation wavelength 650 nm, emission wavelength 670 nm, LED-power 15%, laser-power 80%) using a Monolith NT. 115 Pico (NanoTemper Technologies) at 25° C. in the absence and presence of various concentrations of NAD+, acetylated and de-acetylated peptide (K122-MnSOD peptide). Dissociation constants were determined with GraFit7 (Erithacus Software) by nonlinear fitting using a 1:1 binding model. Each experiment was repeated at least twice.

The specified value of $$\frac{K_{d,NAD+}}{K_{d,NAD+,app}}$$

is 0.50. Direct MST measurements of the binding affinity of Honokiol to apoenzyme ($K_d$=1009.1±128.9 nM), the binding affinity of NAD+ to the apoenzyme ($K_d$=90853.8.±12264.5 nM) and the binding affinity of Honokiol to the enzyme:NAD+ complex ($K_d$=1674.8±125.3 nM) were made. From these data, it is possible to extract the binding affinity of NAD+ to the enzyme:Honokiol complex as well, and hence to estimate the value of $$\frac{K_{d,NAD+}}{K_{d,NAD+,app}}$$

Figure 7A:
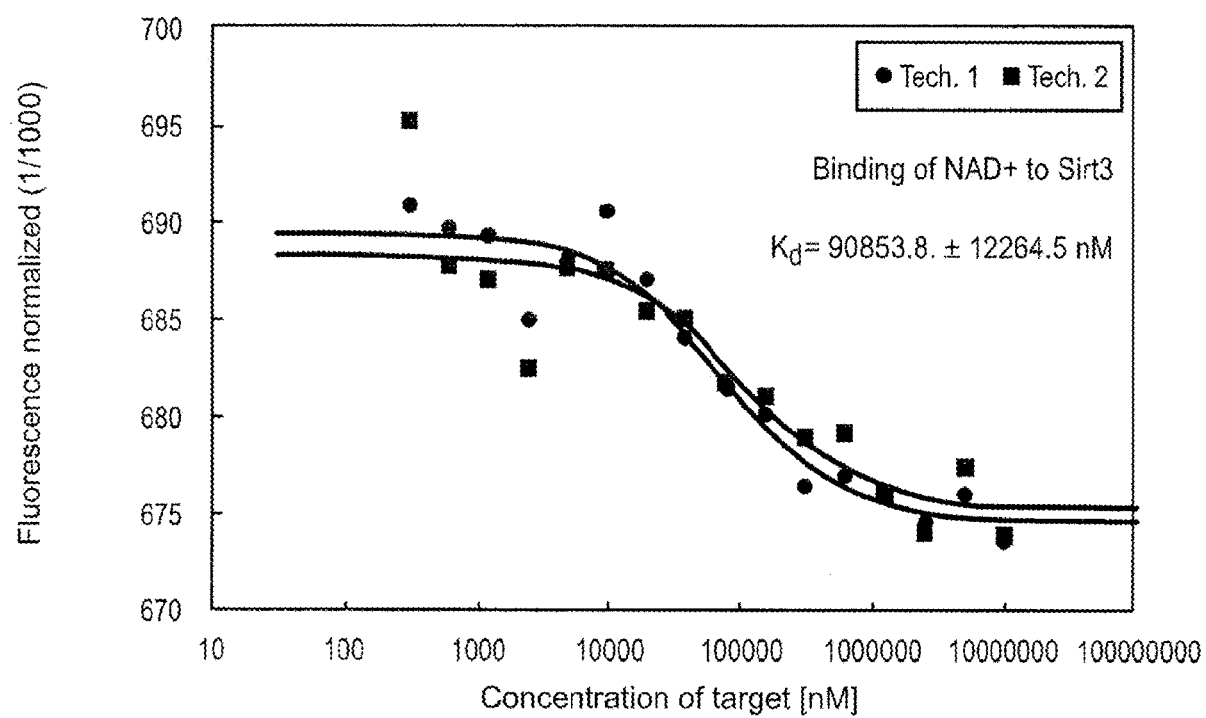
FIGS. 7A-7C. Determination of binding affinities of Honokiol and NAD+ to SIRT3 complexes by microscale thermophoresis.
Figure 7B:
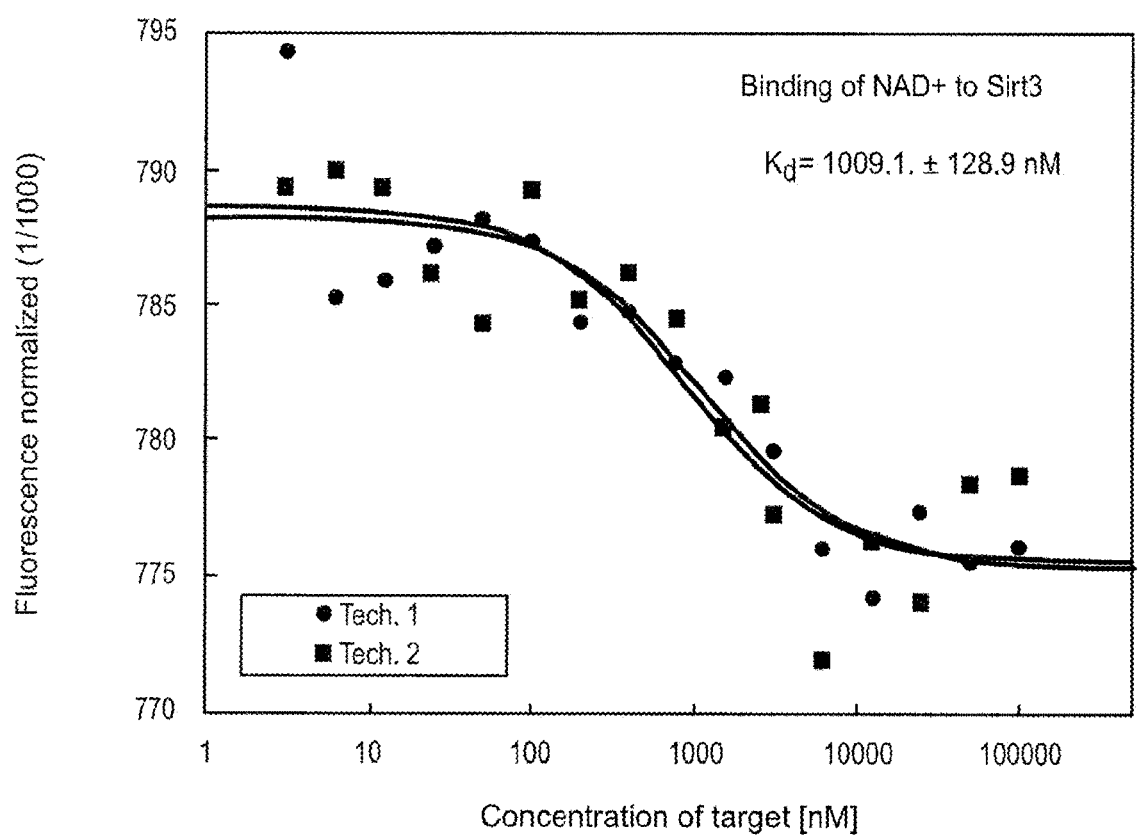
Figure 7C:
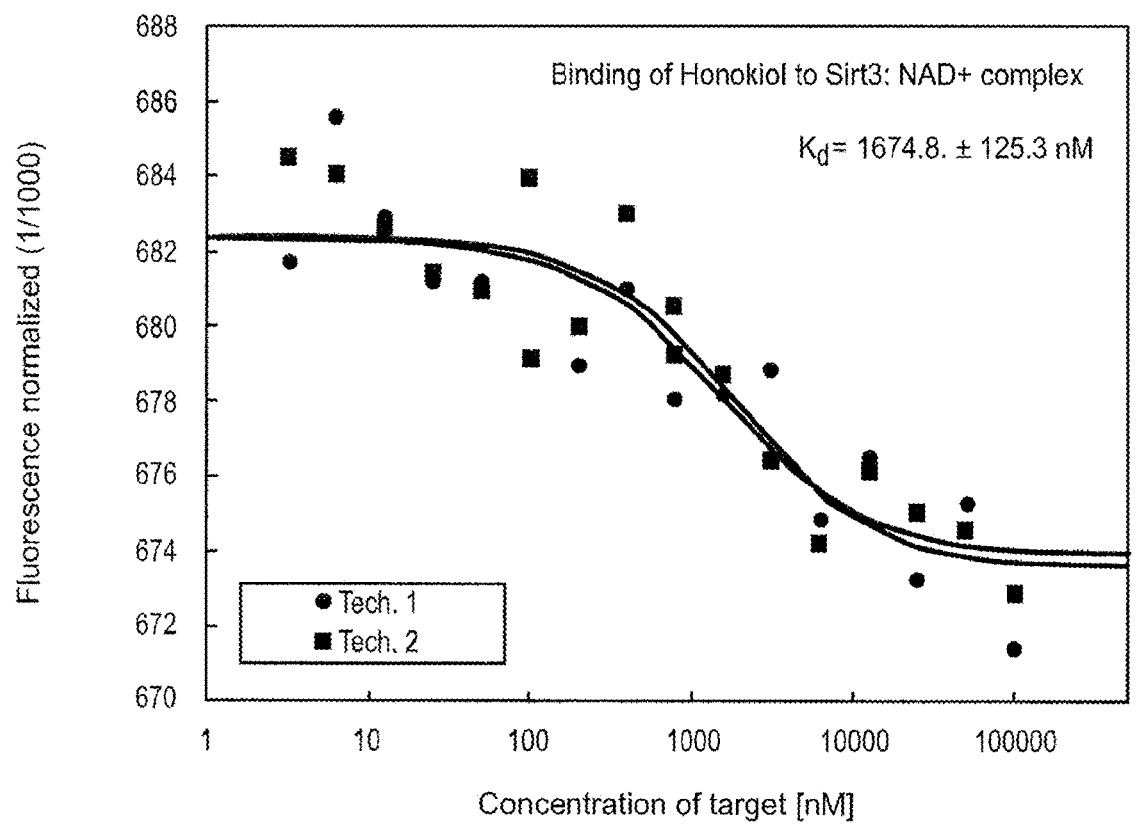

The results are shown in FIG. 7. Since $$K_{d,tot}=K_{d,NAD+}K_{d,honokiol,app}=K_{d,honokiol}K_{d,NAD+,app},$$

we have $$K_{d,NAD+,app}=K_{d,NAD+}K_{d,honokiol,app}/K_{d,honokiol}$$

and as such, $$\frac{K_{d,NAD+}}{K_{d,NAD+,app}}=\frac{K_{d,honokiol}}{K_{d,honokiol,app}}.$$

Thus according to FIG. 7, $$\frac{K_{d,NAD+}}{K_{d,NAD+,app}}=0.60.$$

Since $$\frac{K_{d,NAD+}}{K_{d,NAD+,app}}>$$

the specified threshold value, the test compound is identified as a hit.

Example 3

In a related example, the test compound is isonicotinamide (isoNAM). The sirtuin enzyme and peptide substrate are the same as above. As described above, this test compound would be screened out during hit identification.

Hit Validation

Example 4

The hit compounds in this example are DHP-1 and DHP-2 (N-Benzyl-3,5-dicarboxy-4-phenyl-1,4-dihydropyridine). DHP-1, identified as a hit using the high-throughput fluorimetric assay above, was subsequently subjected to validation using a label-free endpoint kinetic assay at selected substrate concentrations. Similar experiments were carried out on DHP-2.

Label-Free Measurement of the Effect of DHP-1,2 on Sirt3 Deacetylation Activity

Reactions for DHP-2 were performed in triplicate and consisted of 3 mM NAD$^+$ and 10 μM P53 derived synthetic peptide (QPKK$^{AC}$-AMC) or 3 μM NAD$^+$ and 250 μM peptide substrate in presence of different concentrations of DHP-2 (KareBay Biochem, NJ), ranging from 0-400 μM, in a buffer containing 50 mM TRIS-HCl, 137 mM NaCl, 2.7 mM KCl, and 1 mM MgCl2, pH 8.0. The reactions were started by addition of Sirt3 and incubated at 37° C. for 30 minutes. The reactions were terminated by immediately stored in –80° C.

A Beckman System Gold high performance liquid chromatography (HPLC) and a ZORBAX C18 (4.6×250 mm) column were used throughout the study. Components from the enzymatic reaction were separated using gradient system comprising 0.05% aqueous trifluoroacetic acid (solvent A) and acetonitrile containing 0.02% trifluoroacetic acid (solvent B) using a constant flow rate of 1 ml/min. Upon injection of the sample (40 ul), the HPLC was run isocratically in solvent A for 1 min followed by a linear gradient of 0-51% B over a 20-min period with the detector set at 214 nm. The gradient was then increased to 100% solvent B over 10-min period to wash the column, and then re-equilibrated with 100% A. The deacetylated and substrate peptides had retention times of ~12.5 and 14.8 min, respectively. The percent of product produced was calculated by dividing the product peak area over the total area.

Reactions for DHP-1 used a similar protocol, but were carried out at a single concentration of modulator and varying concentrations of NAD+ and fluorolabeled peptide at 37° C. in a 50 μl reaction volume containing 50 mM Tris/Cl (pH=8), 137 mM NaCl, and 5% DMSO. [DHP] was 50 uM.

The following table (Table 2) displays the results of the assay for DHP-1. Note that the label-free assay demonstrates that DHP-1 does not activate SIRT3 under these conditions for the specified threshold value of $v_{app}/v$=1.10.

TABLE 2

| | HPLC-based hit validation of SIRT3 activity modulation by DHP-1. | | | | | |
|---|---|---|---|---|---|---|
| | 100 uM NAD + 100 uM FdL Peptide | | 200 uM NAD + 100 uM FdL Peptide | | 500 uM NAD + 250 uM FdL Peptide | |
| | Control (5% DMSO) | 50 uM DHP-1 in 5% DMSO | Control (5% DMSO) | 50 uM DHP-1 in 5% DMSO | Control (5% DMSO) | 50 uM DHP-1 in 5% DMSO |
| Product Peak Area | 478 | 462 | 791 | 719 | 388 | 394 |
| Substrate Peak Area | 7525 | 7536 | 6923.8 | 6879 | 1791 | 1826 |
| Total Peak Area | 8003 | 7998 | 7714.8 | 7598 | 1830 | 1866 |
| % product formation | 5.973 | 5.776 | 10.253 | 9.463 | 2.121 | 2.111 |
| % Sirt3 Activity | 100.0 | 96.7 | 100.0 | 92.3 | 100.0 | 99.5 |

Figures 8A, 8B, 8C:
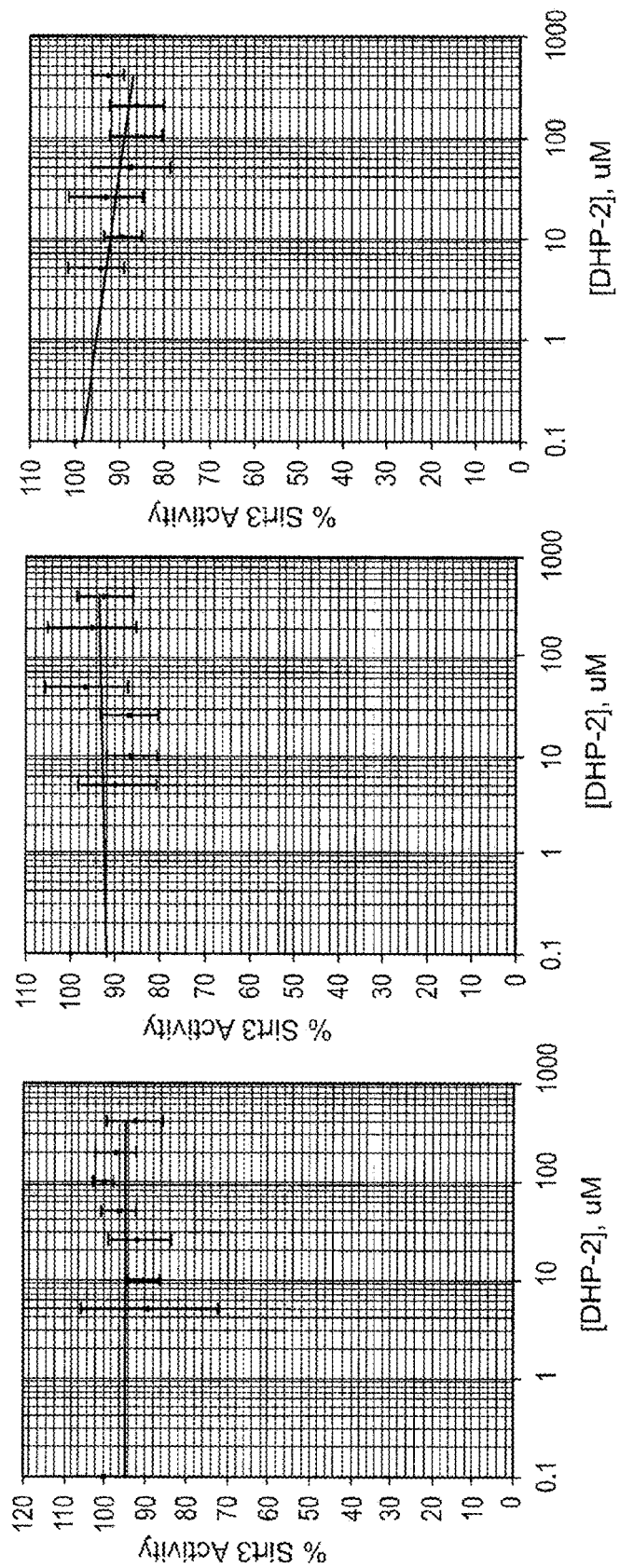
FIGS. 8A-8C. Effect of a dihydropyridine derivative (DHP-2) on Sirt3 deacetylation activity using a label-free assay. Recombinant human SIRT3 was incubated for 30 min at 37° C. in the presence of 0, 5, 10, 25, 50, 100, 200, 400 μM DHP-2.

FIG. 8 displays the results of the assay for DHP-2. Note that the label-free assay demonstrates that DHP-2 does not activate SIRT3 under the conditions of 3 μM NAD+ and 250 μM peptide substrate for the specified threshold value of $v_{app}/v=1.10$.

Thus, the DHP hits identified using the high-throughput fluorimetric assay are not validated by the label-free assay.

Example 5

Honokiol, identified as a hit using MST binding affinity determination above, was subjected to validation using a label-free endpoint kinetic assay.

Label-Free Measurement of the Effect of Honokiol on Sirt3 Deacetylation Activity Reactions were performed in triplicate and consisted of 2.5 mM NAD+ and 6.25 μM MnSOD derived synthetic peptide (KGELLEAIK$^{Ac}$RDFGSFDKF) or 50 μM NAD+ and 600 μM peptide substrate in presence of different concentrations of $^{Honokiol}$ (Catalogue #H4914, Sigma), ranging from 0-200 μM, in a buffer containing 50 mM TRIS-HCl, 137 mM NaCl, 2.7 mM KCl, and 1 mM MgCl2, pH 8.0 and 5% DMSO. The reactions were started by addition of Sirt3 and incubated at 37° C. for 30 minutes. The reactions were terminated by immediately stored in −80° C. An Agilent 1260 infinity high performance liquid chromatography (HPLC) system and a ZORBAX C18 (4.6×250 mm) column were used throughout the study. Components from the enzymatic reaction were separated using gradient system comprising 10% aqueous acetonitrile (solvent A) and acetonitrile containing 0.02% trifluoroacetic acid (solvent B) using a constant flow rate of 1 ml/min. Upon injection of the sample (40 ul), the HPLC was run isocratically in solvent A for 1 min followed by a linear gradient of 0-51% B over a 20-min period with the detector set at 214 nm. The gradient was then increased to 100% solvent B over 10-min period to wash the column, and then re-equilibrated with 100% A. The deacetylated and substrate peptides had retention times of ~15 and 16 min, respectively. The percent of product produced was calculated by dividing the product peak area over the total area.

Figures 9A, 9B:
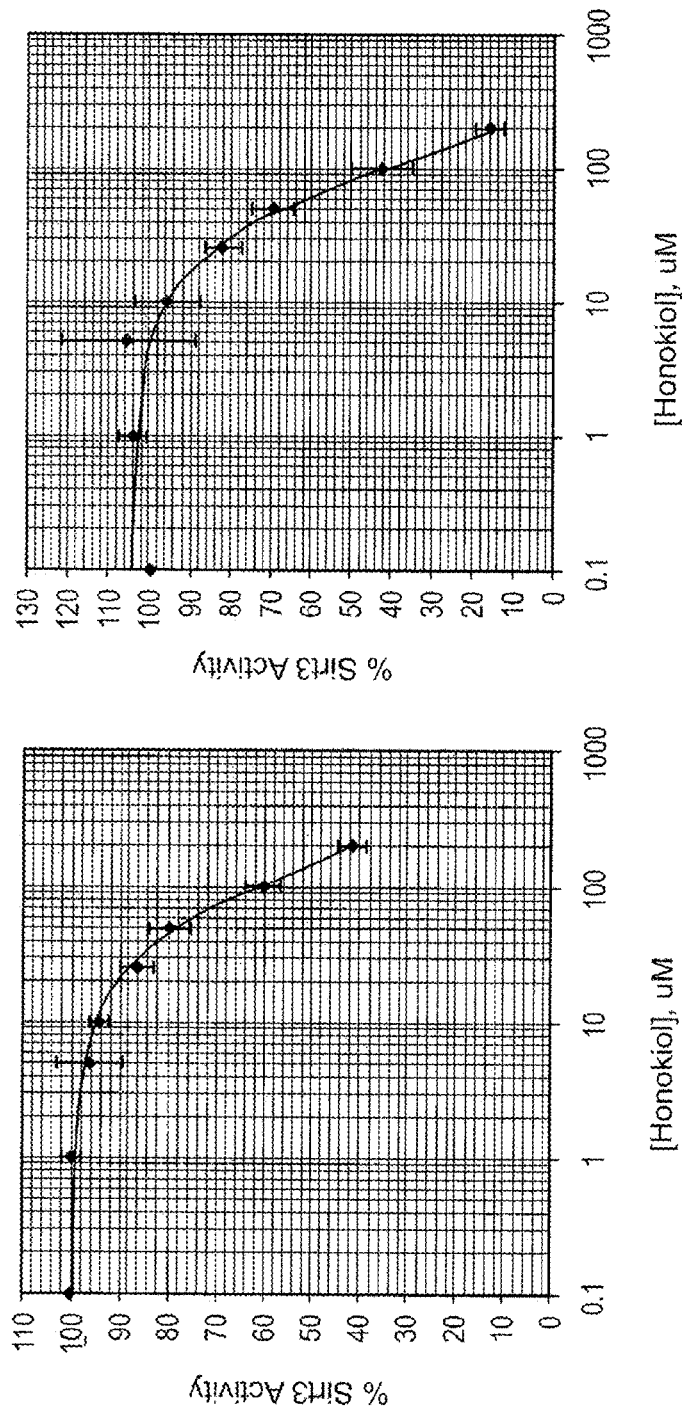
FIGS. 9A and 9B. Effect of Honokiol on Sirt3 deacetylation activity using a label-free assay. Recombinant human SIRT3 was incubated for 30 min at 37° C. in the presence of 0, 1, 5, 10, 25, 50, 100, 200 μM Honokiol.

The results in FIG. 9 show that based on these data, Honokiol at 10 uM is not validated as a hit using the label-free kinetic assay if the particular value of [NAD+] is 50 uM and the specified threshold value of $v_{app}/v=1.10$. More experiments are needed to determine whether it is validated at lower values of $v_{app}/v$.

Hit Evolution

One of the properties improved during hit evolution is a hit compound's solubility. Although DHP-1 was not validated as a hit compound, we use it for the purpose of illustrating the hit mutation process and solubility improvement.

Solubility Measurement

Solubility of DHP-2 and Honokiol in HDAC buffer and 5% DMSO/HDAC were 2.303 and 0.12 mg/ml, respectively. DHP-1 in up to 20% DMSO/HDAC was insoluble. In brief, HPLC (Agilent 1100 series) was used to perform the test. Calibration curves were established using concentration range covering the estimated solubility's. The samples were then analyzed by a well-calibrated HPLC method. The linearity was measured by R-values at least >0.99. The estimated detection limit was around 0.002 mg/mL (2 μg/mL) based on acceptable N/S ratio. Over saturated samples were prepared by dosing excess compounds into the solvent mixtures of interest. The samples were equilibrated at ambient (24-25° C.) for 48 hours and then analyzed by the same HPLC method.

DHP-1 (FIG. 6A) can be dissolved in reaction buffer at 50 uM, but only in the form of a metastable solution. Measurement of DHP-1's solubility using the above protocol revealed that it is thermodynamically insoluble.

Figure 6B:
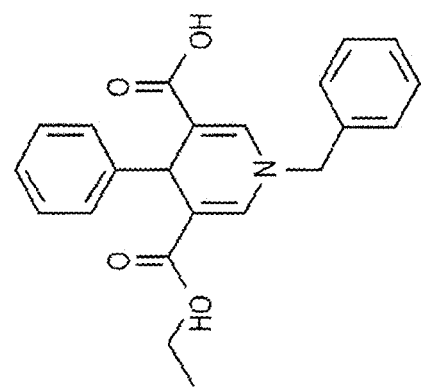
Figure 6A:
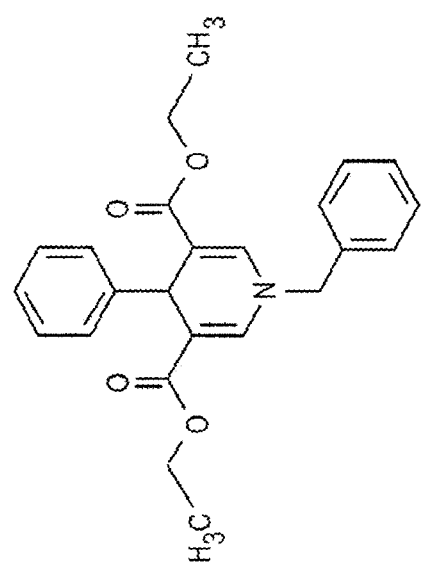

By mutating the ester groups in DHP-1 to carboxylic acid groups, we obtain the mutated compound DHP-2 (FIG. 6B). In contrast to DHP-1, DHP-2 is thermodynamically soluble (Table 3):

TABLE 3

Solubility of DHP-2 in different % DMSO/HDAC solution.

| Compound | Solvent | AUC | Solubility (mg/mL) |
|---|---|---|---|
| 1-benzyl-phenyl- | 100% HDAC | 21397 | 2.303 |
| 1,4-dihydropyridine- | 2% DMSO | 16212 | 1.745 |
| 3,5-dicarboxylic acid | 5% DMSO | 19867 | 2.138 |
| (DHP2) | 10% DMSO | 20392 | 2.195 |

The solubility of Honokiol was also assessed with this protocol (Table 4):

TABLE 4

Solubility of Honokiol in different % DMSO/HDAC solution.

| Compound | Solvent | AUC | Solubility (mg/mL) |
|---|---|---|---|
| Honokiol | 100% HDAC | n.d. | n.d. |
|  | 1% DMSO | n.d. | n.d. |
|  | 2% DMSO | 260.8 | 0.041 |
|  | 5% DMSO | 766.2 | 0.120 |

In order to illustrate how to determine whether a mutated hit compound constitutes a lead for a MB-STAC, we refer to the activity data reported above for DHP-2 and Honokiol, although these compounds were not validated as hits based on the threshold values specified above.

Comparing the activity results for DHP-2 using the label-free assay (FIG. 8) with the theoretical predictions of the extent of activity enhancement for three different levels of $K_{m,NAD+}$ reduction (FIG. 10), we see that DHP-2 at any concentration tested does not induce a rate enhancement exceeding those predicted at any of the three levels of $K_{m,NAD+}$ reduction depicted.

TABLE 5

Effect of Km reduction by a sirtuin activating compound on deacylation rate at specified values of NAD+ concentration as a fraction of $K_m$. The table assumes that $v_{max}$ is not altered by the compound. x denotes $K_{m,NAD+,app}/K_{m,NAD+}$ whereas y denotes [NAD+]/$K_{m,NAD}$; The boldfaced line indicates the value of [NAD+] that was used in the experiments with DHP-2. Km of NAD+ can change with peptide substrate; it is estimated to equal 2000 uM for FdL2 peptide substrate.

| [NAD+], | Km, NAD+ = 2000 μM y = [NAD+]/ | $v_{app}/v$ | | |
|---|---|---|---|---|
| μM | Km, NAD+ | x = 0.7 | x = 0.8 | x = 0.9 |
| 10 | 0.005 | 1.426 | 1.248 | 1.110 |
| 50 | 0.025 | 1.4138 | 1.2424 | 1.1081 |
| 2500 | 1.25 | 1.1538 | 1.0976 | 1.0465 |
| 3000 | 1.5 | 1.1364 | 1.087 | 1.0417 |

Similarly, comparing the activity results for Honokiol using the label-free assay (FIG. 9) with the theoretical predictions of the extent of activity enhancement for three different levels of $K_{m,NAD+}$ reduction, we see that Honokiol at 10 uM does not activate SIRT3 under these conditions for specified values of $K_{m,NAD+,app}/K_{m,NAD+}=0.7$ or 0.8. More experiments are needed to validate the hit for $K_{m,NAD+,app}/K_{m,NAD+}=0.9$.

TABLE 6

Effect of $K_m$ reduction by a sirtuin activating compound on deacylation rate at specified values of NAD+ concentration as a fraction of $K_m$. The table assumes that $v_{max}$ is not altered by the compound. x denotes $K_{m,NAD+,app}/K_{m,NAD+}$ whereas y denotes $[NAD+]/K_{m,NAD}$. The boldfaced line indicates the value of [NAD+] that was used in the experiments with Honokiol. Km of NAD+ can change with peptide substrate; since Km, NAD+ is not known for MnSOD peptide substrate, the known Km, NAD+ for another physiological substrate of SIRT3, namely AceC S2, is used instead.

| [NAD+], µM | Km, NAD+ = 600 µM y = [NAD+]/Km, NAD+ | x = 0.7 | x = 0.8 | x = 0.9 |
|---|---|---|---|---|
| 50 | 0.0833 | 1.383 | 1.226 | 1.102 |
| 100 | 0.0167 | 1.346 | 1.207 | 1.094 |

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method for identifying a test compound for a mechanism-based sirtuin activating compound (MB-STAC), the method comprising:
    establishing a library of compounds on the basis of the compounds exhibiting computational docking with at least one sirtuin complex selected from the group consisting of sirtuin+peptide substrate complex, sirtuin+peptide substrate+NAD$^+$ complex, sirtuin+alkylimidate intermediate+NAM complex, sirtuin+alkylimidate complex, and sirtuin+O-AADPR complex; and
    a) incubating the test compound with a sirtuin enzyme, NAD$^+$, NAM, and a saturating concentration of an acylated substrate peptide in an assay for deacylation activity;
    b) measuring non-steady state ($v_{non-ss}$) and steady state (v) rate of sirtuin enzyme-catalyzed deacylation at several NAD$^+$ concentrations for each of several NAM concentrations; and
    c) determining whether the test compound is a hit compound.

2. The method of claim 1, wherein compounds of the library exhibiting computational docking with the sirtuin+peptide substrate+NAD$^+$ complex are identified as test compounds.

3. The method of claim 1, wherein compounds of the library exhibiting computational docking with the sirtuin+peptide substrate+NAD$^+$ complex and engaging in binding interactions with the sirtuin cofactor binding loop are identified as test compounds.

4. The method of claim 1, wherein a compound of the library is identified as test compound if the compound:
    a) exhibits computational docking with at least one of the sirtuin+peptide substrate+NAD$^+$ complex and sirtuin+alkylimidate intermediate+NAM complex; and
    b) ratios of dissociation constants for binding of the compound to the sirtuin+peptide substrate complex, sirtuin+peptide substrate+NAD$^+$ complex, sirtuin+alkylimidate intermediate+NAM complex, and sirtuin+alkylimidate complex, denoted by $K_{d1,A}$; $K_{d2,A}$; $K_{d3,A}$; and $K_{d4,A}$ respectively, satisfy at least one of the following relations:

$$\frac{K_{d1,A}}{K_{d2,A}} \leq 1 \Leftrightarrow \frac{K'_{d,NAD+}}{K_{d,NAD+}} \geq 1$$

$$\frac{K_{d2,A}}{K_{d3,A}} \gg 1 \Leftrightarrow \frac{K'_{ex}}{K_{ex}} \ll 1$$

$$\frac{K_{d3,A}}{K_{d4,A}} \geq 1 \Leftrightarrow \frac{K'_{d,NAM}}{K_{d,NAM}} \geq 1$$

wherein $\Leftrightarrow$ means equivalent to, wherein $K_{d,NAD+}$ is the dissociation constant for NAD$^+$, $K_{d,NAM}$ is the dissociation constant for NAM, and $K_{ex}$ is the exchange equilibrium constant, wherein the ' sign denotes corresponding values in presence of the test compound, and wherein $K_{d1,A}$, $K_{d2,A}$, $K_{d3,A}$, and $K_{d4,A}$ are estimated via the computational docking.

5. The method of claim 1, wherein a compound of the library is identified as test compound if dissociation constants for binding of the selected compound to the sirtuin+peptide substrate complex, sirtuin+peptide substrate+NAD$^+$ complex, sirtuin+alkylimidate intermediate complex, and sirtuin+O-AADPR complex, denoted by $K_{d1,A}$; $K_{d2,A}$; $K_{d4,A}$; and $K_{d5,A}$ respectively, satisfy the following relations:
    $K_{d2,A}$ or $K_{d4,A}$ are less than predetermined threshold values; and
    $K_{d1,A}$ or $K_{d5,A}$ are greater than a predetermined threshold values,
wherein $K_{d1,A}$, $K_{d2,A}$, $K_{d4,A}$, and $K_{d5,A}$ are estimated via the computational docking.

6. The method of claim 1 further comprising assaying effects of the test compound on sirtuin non-steady state, steady-state and equilibrium parameters, the method comprising:
    d) fitting following nonlinear model to steady state rate data:

$$\frac{v}{v_{max}} = \frac{[NAD^+]\left(1 + \frac{[NAM]}{K_1}\right)}{K_{m,NAD+}\left(1 + \frac{[NAM]}{K_2}\right) + [NAD^+]\left(1 + \frac{[NAM]}{K_3}\right)}$$

wherein v denotes initial deacylation rate;
    e) obtaining estimates of steady state parameters $v_{max}$, $K_{m,NAD+}$, $K_1$, $K_2$, $K_3$ in the absence of the test compound and $v_{max,app}$, $K_{m,NAD+,app}$, $K_{1,app}$, $K_{2,app}$, $K_{3,app}$ in the presence of the test compound at a nonzero concentration;
    f) applying a relationship between the steady state parameters estimated in (d) and at least one of the following properties of the sirtuin enzyme:

$K_{d,NAD+}$, $K_{d,NAM}$, $K_{ex}$, $k_1$, $k_{-1}$, $k_2$, $k_{-2}$, $k_{ex}$, $k_{-ex}$, $k_{cat}$ wherein $K_{d,NAD+}$ is the dissociation constant for NAD, $K_{d,NAM}$ is the dissociation constant for NAM, $K_{ex}$ is the exchange equilibrium constant, $k_1, k_{-1}$ are the on/off rate constants of $NAD^+$ binding to enzyme-peptide substrate complex, $k_2, k_{-2}$ are the on/off rate constants of NAM binding, $k_{ex}, k_{-ex}$ are the nicotinamide cleavage and base exchange rate constants, and $k_{cat}$ is the rate constant of the rate limiting step of subsequent steps of deacylation and product/coproduct release; and g) experimentally measuring the dissociation constants for binding of the compound to the sirtuin+peptide substrate complex, sirtuin+peptide substrate+NAD$^+$ complex, sirtuin+thioalkylimidate intermediate complex, and sirtuin+O-AADPR complex, denoted by $K_{d1,A}$; $K_{d2,A}$; $K_{d4,A}$; and $K_{d5,A}$ respectively.

7. The method of claim 1, wherein $v_{non-ss}$ is measured at one or more times when concentration of the product is less than sirtuin enzyme concentration.

8. The method of claim 7, wherein the test compound is a hit compound if $v_{non-ss}$ is greater in presence of the test compound than $v_{non-ss}$ in absence of the test compound.

9. The method of claim 1, wherein $v_{non-ss}$ is measured under conditions where sirtuin enzyme concentration is greater than remaining concentration of the acylated peptide substrate.

10. The method of claim 9, wherein the wherein the test compound is a hit compound if $v_{non-ss}$ is greater in presence of the test compound than $v_{non-ss}$ in absence of the test compound.

11. The method of claim 6 wherein the relationship is selected from the following:

$$v_{max} \approx k_{cat}[E]_0$$

$$K_{m,NAD^+} \approx k_{cat}\left(\frac{1}{k_1} + K_{d,NAD+} \frac{k_{-2} + k_{-ex}}{k_{-2} k_{ex}}\right)$$

$$\frac{1}{K_1} \approx \frac{1}{K_{d,NAM}}$$

$$\frac{1}{K_2} \approx \frac{K_{d,NAD^+} K_{ex}}{K_{m,NAD^+} K_{d,NAM}}$$

$$\frac{1}{K_3} = \frac{1}{\alpha K_2} \approx \frac{1 + K_{ex}}{K_{d,NAM}}$$

wherein $[E]_0$ denotes the total sirtuin enzyme concentration, wherein the relationship relates the steady state parameters of the sirtuin enzyme to the dissociation, equilibrium and rate constants of the deacylation.

12. The method of claim 11 where the test compound is a hit compound if the value of
$\alpha * K_{m,NAD+}$ in the presence of the test compound is less than its value in absence of the test compound.

13. The method of claim 11 where the test compound is a hit compound if the value of
$K_{d,NAM}$ in the presence of the test compound is higher than its value in absence of the test compound.

14. The method of claim 11 where the test compound is a hit compound if the value of
$K_{ex}$ in the presence of the test compound is lower than its value in absence of the test compound.

15. The method of claim 6 where the test compound is a hit compound if $K_{d2,A}$ or $K_{d4,A}$ are less than predetermined threshold values; and $K_{d1,A}$ or $K_{d5,A}$ are greater than predetermined threshold values.

16. The method of claim 6 where the dissociation constants are measured by either microscale thermophoresis or isothermal calorimetry.

17. The method of claim 1, wherein the test compound is generated from a database of drug-like compounds.

18. The method of claim 10, wherein the test compound is a hit compound if the net effect on steady state catalytic turnover is inhibition ($v_{app} < v$) or activation ($v_{app} > v$).

19. The method of claim 18, wherein the net effect on catalytic turnover is inhibition and the net inhibitory effect is associated with the hit compound decreasing $$1/K_3 \approx \frac{1 + K_{ex}}{K_{d,NAM}}$$

but increasing $K_{m,NAD^+}$, due to a concurrent increase in $K_{d,NAD^+}$.

20. A method for identifying a test compound for a mechanism-based sirtuin activating compound (MB-STAC), the method comprising:
establishing a library of compounds on the basis of the compounds exhibiting computational docking with at least one sirtuin complex selected from the group consisting of sirtuin+peptide substrate complex, sirtuin+peptide substrate+NAD$^+$ complex, sirtuin+alkylimidate intermediate+NAM complex, sirtuin+alkylimidate complex, and sirtuin+O-AADPR complex, wherein the test compound is generated from a database of drug-like compounds.

* * * * *